United States Patent
Devengenzo et al.

(10) Patent No.: US 11,766,303 B2
(45) Date of Patent: Sep. 26, 2023

(54) ACTIVE AND SEMI-ACTIVE DAMPING

(71) Applicant: INTUITIVE SURGICAL OPERATIONS, INC., Sunnyvale, CA (US)

(72) Inventors: Roman L. Devengenzo, San Jose, CA (US); Bruce M. Schena, Menlo Park, CA (US); David W. Robinson, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/080,577

(22) Filed: Dec. 13, 2022

(65) Prior Publication Data

US 2023/0114914 A1     Apr. 13, 2023

Related U.S. Application Data

(63) Continuation of application No. 17/558,153, filed on Dec. 21, 2021, now Pat. No. 11,547,506, which is a continuation of application No. 16/995,716, filed on Aug. 17, 2020, now Pat. No. 11,234,782, which is a continuation of application No. 16/102,614, filed on Aug. 13, 2018, now Pat. No. 10,779,902, which is a continuation of application No. 14/814,858, filed on Jul. 31, 2015, now Pat. No. 10,058,395.

(60) Provisional application No. 62/032,490, filed on Aug. 1, 2014.

(51) Int. Cl.
*A61B 34/37*     (2016.01)
*A61B 17/00*     (2006.01)
*A61B 90/00*     (2016.01)

(52) U.S. Cl.
CPC .... *A61B 34/37* (2016.02); *A61B 2017/00075* (2013.01); *A61B 2090/064* (2016.02)

(58) Field of Classification Search
CPC .............. A61B 34/37; A61B 2090/064; A61B 2017/00075
See application file for complete search history.

(56) References Cited

U.S. PATENT DOCUMENTS

| | | |
|---|---|---|
| 5,184,601 A | 2/1993 | Putman |
| 5,341,078 A | 8/1994 | Torii et al. |
| 5,432,417 A | 7/1995 | Takenaka et al. |
| 5,445,166 A | 8/1995 | Taylor et al. |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — David M Fenstermacher
(74) *Attorney, Agent, or Firm* — Artegis Law Group, LLP

(57) ABSTRACT

Techniques for active and semi-active damping include a system including a processor and a linkage having a first link, a second link, and a damper coupling the second link to the first link. The processor is configured to receive a movement command for moving the linkage; determine one or more first vibrations expected to occur in the linkage as a result of performing the movement command; determine a movement profile for moving the linkage to reduce the one or more first vibrations; and drive, using a drive component, the linkage to move according to the movement profile.

20 Claims, 21 Drawing Sheets

(56) References Cited

U.S. PATENT DOCUMENTS

| | | |
|---|---|---|
| 5,575,597 A | 11/1996 | Bailey et al. |
| 5,800,423 A | 9/1998 | Jensen et al. |
| 5,808,665 A | 9/1998 | Green et al. |
| 5,855,583 A | 1/1999 | Wang et al. |
| 6,246,200 B1 | 6/2001 | Blumenkranz et al. |
| 6,459,926 B1 | 10/2002 | Nowlin et al. |
| 6,676,669 B2 | 1/2004 | Charles et al. |
| 6,702,805 B1 | 3/2004 | Stuart et al. |
| 6,758,843 B2 | 7/2004 | Jensen et al. |
| 6,786,896 B1 | 9/2004 | Madhani et al. |
| 6,788,018 B1 | 9/2004 | Blumenkranz |
| 7,155,316 B2 * | 12/2006 | Sutherland ............ A61B 34/37 901/1 |
| 7,594,912 B2 | 9/2009 | Cooper et al. |
| 7,763,015 B2 | 7/2010 | Cooper et al. |
| 8,494,613 B2 | 7/2013 | Markowitz et al. |
| 8,527,094 B2 | 9/2013 | Kumar et al. |
| 8,944,070 B2 | 2/2015 | Guthart et al. |
| 9,480,534 B2 | 11/2016 | Bowling et al. |
| 9,492,235 B2 | 11/2016 | Hourtash et al. |
| 9,666,101 B2 | 5/2017 | Kumar et al. |
| 9,717,563 B2 | 8/2017 | Tognaccini et al. |
| 9,786,203 B2 | 10/2017 | Wang et al. |
| 9,827,059 B2 | 11/2017 | Robinson et al. |
| 9,867,671 B2 | 1/2018 | Kumar et al. |
| 9,888,973 B2 | 2/2018 | Olson et al. |
| 10,058,395 B2 | 8/2018 | Devengenzo et al. |
| 10,225,656 B1 | 3/2019 | Kratz et al. |
| 10,517,692 B2 | 12/2019 | Eyre et al. |
| 10,710,241 B2 | 7/2020 | Oyama et al. |
| 10,779,902 B2 | 9/2020 | Devengenzo et al. |
| 10,945,904 B2 | 3/2021 | De Jesus Ruiz |
| 11,007,021 B2 | 5/2021 | Walker et al. |
| 11,020,016 B2 | 6/2021 | Wallace et al. |
| 11,037,464 B2 | 6/2021 | Ho et al. |
| 11,173,614 B2 | 11/2021 | Adachi et al. |
| 11,179,213 B2 | 11/2021 | Huang et al. |
| 11,192,244 B2 | 12/2021 | Nakamura et al. |
| 11,234,782 B2 | 2/2022 | Devengenzo et al. |
| 11,305,424 B2 | 4/2022 | Yamane |
| 11,357,586 B2 | 6/2022 | Huang et al. |
| 11,382,650 B2 | 7/2022 | Noonan et al. |
| 11,464,590 B1 * | 10/2022 | Roh ............ A61B 17/1626 |
| 2008/0235970 A1 | 10/2008 | Crampton |
| 2013/0116706 A1 | 5/2013 | Lee et al. |
| 2014/0222207 A1 | 8/2014 | Bowling et al. |
| 2014/0277741 A1 * | 9/2014 | Kwon .................. B25J 9/1689 700/263 |
| 2015/0204480 A1 | 7/2015 | Lorimer et al. |
| 2016/0030118 A1 | 2/2016 | Devengenzo et al. |
| 2016/0030119 A1 * | 2/2016 | Devengenzo ......... A61B 34/37 606/130 |
| 2018/0079090 A1 | 3/2018 | Koenig et al. |
| 2019/0143506 A1 | 5/2019 | Rabindran et al. |
| 2019/0143513 A1 | 5/2019 | Rabindran et al. |
| 2019/0201044 A1 * | 7/2019 | Shelton, IV ... A61B 17/320092 |
| 2019/0381664 A1 * | 12/2019 | Whitman ............... B25J 9/1671 |
| 2020/0170732 A1 * | 6/2020 | Patriciu ................ A61B 34/20 |
| 2021/0052335 A1 * | 2/2021 | Shuma .................. A61B 34/37 |
| 2021/0169581 A1 * | 6/2021 | Calloway .............. A61B 34/30 |
| 2022/0104986 A1 * | 4/2022 | Ushpizin .............. A61B 34/37 |
| 2022/0117685 A1 | 4/2022 | Devengenzo et al. |
| 2022/0192701 A1 * | 6/2022 | Junio .................... A61B 90/03 |
| 2022/0258333 A1 * | 8/2022 | Gao ......................... B25J 3/00 |
| 2023/0014033 A1 * | 1/2023 | Tojo ...................... A61B 34/75 |

\* cited by examiner

ACTIVE AND SEMI-ACTIVE DAMPING

RELATED APPLICATIONS

This patent application is a continuation of U.S. patent application Ser. No. 17/558,153 filed Dec. 21, 2021, which is a continuation of U.S. patent application Ser. No. 16/995,716 filed Aug. 17, 2020, which is a continuation of U.S. patent application Ser. No. 16/102,614 filed Aug. 13, 2018 and issued as U.S. Pat. No. 10,779,902, which is a continuation of U.S. patent application Ser. No. 14/814,858 filed Jul. 31, 2015 and issued as U.S. Pat. No. 10,058,395, and claims priority to and the benefit of the filing date of U.S. Provisional Patent Application 62/032,490, entitled "ACTIVE AND SEMI-ACTIVE DAMPING IN A TELE-SURGICAL SYSTEM," filed Aug. 1, 2014, each of which is incorporated by reference herein in its entirety.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive teleoperated robotic surgical or telesurgical systems have been developed to increase a surgeon's dexterity and avoid some of the limitations on traditional minimally invasive techniques. In telesurgery, the surgeon uses some form of remote control (e.g., a servomechanism or the like) and computer assistance to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the slave servo-mechanically operated instruments.

The servomechanism system used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a teleoperated robotic surgical system is the DA VINCI® Surgical System commercialized by Intuitive Surgical, Inc. of Sunnyvale, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; the full disclosures of which are incorporated herein by reference.

A variety of structural arrangements can also be used to support and position the robotic surgical manipulator and the surgical instrument at the surgical site during robotic surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, the full disclosures of which are incorporated herein by reference.

While the new telesurgical systems and devices have proven highly effective and advantageous, still further improvements are desirable. In general, improved minimally invasive robotic surgery systems are desirable. It would be particularly beneficial if these improved technologies enhanced the efficiency and ease of use of robotic surgical systems. For example, it would be particularly beneficial to increase maneuverability, improve space utilization in an operating room, provide a faster and easier set-up, inhibit collisions between robotic devices during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

One aspect of the present disclosure relates to a damped surgical system. The damped surgical system includes a base, a surgical tool, and a linkage supporting the surgical tool relative to the base. In some embodiments, the linkage includes a series of arms with a plurality of joints disposed between adjacent arms so that commanded movements of the surgical tool relative to the base are effected by articulation of the joints. In some embodiments, one of the joints includes a first arm portion connected to a mount, a second arm portion having a first end connected to the mount via the first arm portion and a second end connected to the surgical tool, a sensor that can be an acceleration sensor that detects an acceleration or a position sensor that detects a position of the linkage, and a damper positioned between the first arm portion and a second arm portion. In some embodiments, the damped surgical system incudes a processor that can receive a signal from the sensor and that can control a variable portion of the damper according to the received signal. In some embodiments, the inertial properties of the linkage can change based on the position of the linkage. Thus, in some embodiments, the damped surgical system incudes a processor that can receive a signal from the acceleration sensor and a signal from the position sensor, that can calculate one or several inertial properties of the linkage based on those signals, and that can control a variable portion of the damper according to the received signals.

In some embodiments, the damper can include a spring element and a variable damping element. In some embodiments, the damping coefficient of the variable damping element is changed in response to the control by the processor.

In some embodiments, the damper can include a 3 DOF damping platform. In some embodiments, the 3 DOF damping platform can have a top plate and a bottom plate connected by an flexure, which can be a torsional/bending flexure, and a plurality of variable dampers radially positioned around the flexure. In some embodiments, the top plate and the bottom plate of the 3 DOF damping platform can be connected by a radial flexure that includes a baseplate and a plurality of vertical walls extending from the baseplate to the top plate. In some embodiments, the damped surgical system includes a decoupling flexure between the flexure and the radial flexure.

In some embodiments, the 3 DOF damping platform can include a top plate and a bottom plate connected by a shaft cantilevered to the bottom plate and connected to the top plate via a ball pivot. In some embodiments, the 3 DOF damping platform further includes a plurality variable dampers radially positioned around the shaft.

In some embodiments, at least one of the plurality of variable dampers is paired with a spring, and in some embodiments, at least one of the plurality of variable dampers can include at least one coil-over spring.

One aspect of the present disclosure relates to a method for damping vibration in a surgical system. The method can include positioning a robotic linkage base adjacent to a patient for a surgical proceeding, and positioning a first surgical tool and a second surgical tool proximate to the patient, the first surgical tool supported relative to the robotic linkage base by a first arm. In some embodiments, a proximal end of the first arm is connected to the robotic linkage base via a first damper and in some embodiments, a distal end of the first arm connects to a first surgical tool. In some embodiments, the second surgical tool can be supported relative to the robotic linkage base by a second arm having a proximal end that is connected to the robotic linkage base via a second damper and a distal end that is connected to the second surgical tool. The method can include directing a movement of the first arm, which movement of the first arm creates vibrations, sensing an acceleration in the first arm with a sensor located on the first arm, which acceleration characterizes at least one of the movement of the first arm and the vibrations created by the movement of the first arm, and adjusting a damping property of a variable component of one of the first and second dampers so as to inhibit uncommanded movement of the second tool.

In some embodiments, the method includes determining whether to adjust the damping property of the variable component of one of the first and second dampers by comparing the sensed acceleration to a first, predicted value to identify a vibration, and in some embodiments, the method can further include determining whether to adjust the damping property of the variable component of one of the first and second dampers by comparing the identified vibration to a second value to determine, for example, if the magnitude of the vibration warrants damping. In some embodiments, the first, predicted value can identify an expected acceleration based on a received command for movement of the first arm. This predicted value can be based on one or several known dynamic/inertial properties of the first arm. In some embodiments, the method includes identifying the axes for which to adjust the damping property of the variable component of one of the first and second dampers. In some embodiments, the method includes generating a damping solution, which damping solution identifies the variable component for adjustment and identifies the adjustment of the variable component.

In some embodiments, one of the first and second dampers can include a spring element and an variable damping element. In some embodiments, one of the first and second dampers can include a 3 DOF damping platform having a top plate and a bottom plate connected by an flexure and a plurality of damping elements positioned around the flexure, which positioning of the damping elements can be radial around the flexure. In some embodiments, the top plate and the bottom plate of the 3 DOF damping platform are connected by a radial flexure comprising a baseplate and a plurality of vertical walls extending from the baseplate to the top plate. In some embodiments, a decoupling flexure can be positioned between the flexure and the radial flexure. In some embodiments the 3 DOF damping platform includes a top plate and a bottom plate connected by a shaft cantilevered to the bottom plate and connected to the top plate via a ball pivot.

One aspect of the present disclosure relates to a damped surgical system. The damped surgical system includes a base, a surgical tool, and a linkage supporting the surgical tool relative to the base, the linkage including a series of arms with a plurality of joints disposed between adjacent arms so that commanded movements of the surgical tool relative to the base are effected by articulation of the joints. In some embodiments, one of the joints includes a first arm portion connected to the base, a second arm portion having a first end connected to the base via the first arm portion and a second end connected to the surgical tool, and a damper. In some embodiments, the damped surgical system incudes a processor that can receive generate a signal to control a movement of the at least one arm, which processor can determine vibrations arising from the movement of the arm, and which processor can control an variable portion of the damper according to the determined vibrations.

In some embodiments, the damper can include a spring element and an variable damping element. In some embodiments, the damping coefficient of the variable damping element is changed in response to the control by the processor. In some embodiments, the damper includes 3 DOF damping platform having a top plate and a bottom plate connected by an flexure and a plurality of dampers radially positioned around the flexure.

In some embodiments, the top plate and the bottom plate of the 3 DOF damping platform are connected by a radial flexure including a baseplate and a plurality of vertical walls extending from the baseplate to the top plate. In some embodiments, the damped surgical system can include a decoupling flexure between the flexure and the radial flexure. In some embodiments, the 3 DOF damping platform can include a top plate and a bottom plate connected by a shaft cantilevered to the bottom plate and connected to the top plate via a ball pivot. In some embodiments, the 3 DOF damping platform can include a plurality damping elements radially positioned around the shaft.

One aspect of the present disclosure relates to a method for damping vibration in a surgical system. The method includes positioning a robotic linkage base adjacent to a patient for a surgical proceeding, and positioning a surgical tool proximate to the patient, the first surgical tool supported relative to the robotic linkage base by an arm. In some embodiments, a proximal end of the arm can connect to the robotic linkage base via a damper and a distal end of the arm can connect to a surgical tool, In some embodiments, the method includes generating a control signal to direct a movement of the surgical tool, determining estimated vibrations arising from the movement of the surgical tool, adjusting a damping property of the damper according to the estimated vibrations, and controlling the movement of the arm according to the generated control signal.

In some embodiments, the method includes determining whether to adjust the damping property of the variable component of the damper by comparing the estimated vibrations to a threshold value. In some embodiments, the method includes identifying the axes for which to adjust the damping property of the variable component of the damper. In some embodiments, the method includes generating a damping solution, which damping solution identifies the variable component for adjustment and identifies the adjustment of the variable component.

In some embodiments of the method, the damper includes a spring element and a variable damping element. In some embodiments of the method, the damper includes a 3 DOF damping platform having a top plate and a bottom plate connected by an flexure and a plurality of dampers radially positioned around the flexure. In some embodiments, the top plate and the bottom plate of the 3 DOF damping platform are connected by a radial flexure including a baseplate and a plurality of vertical walls extending from the baseplate to the top plate. In some embodiments of the method, the damper can include a decoupling flexure between the flexure and the radial flexure. In some embodiments, the 3 DOF damping platform can include a top plate and a bottom plate connected by a shaft cantilevered to the bottom plate and connected to the top plate via a ball pivot.

One aspect of the present disclosure relates to a method for damping vibration in a surgical system. The method includes positioning a robotic linkage base adjacent to a patient for a surgical proceeding, positioning a surgical tool proximate to the patient, the first surgical tool supported relative to the robotic linkage base by an arm. In some embodiments, a proximal end of the arm is connected to the robotic linkage base via a damper and a distal end of the arm connects to a surgical tool. The method can include receiving a movement command requesting a movement of the surgical tool from a first position to a second position, determining an estimated vibration arising from the movement of the surgical tool, generating a movement profile, which movement profile controls the movement of the surgical tool from the first position to the second position and mitigates the estimated vibration, and controlling the movement of the surgical tool according to the generated movement profile.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

Figure 1:
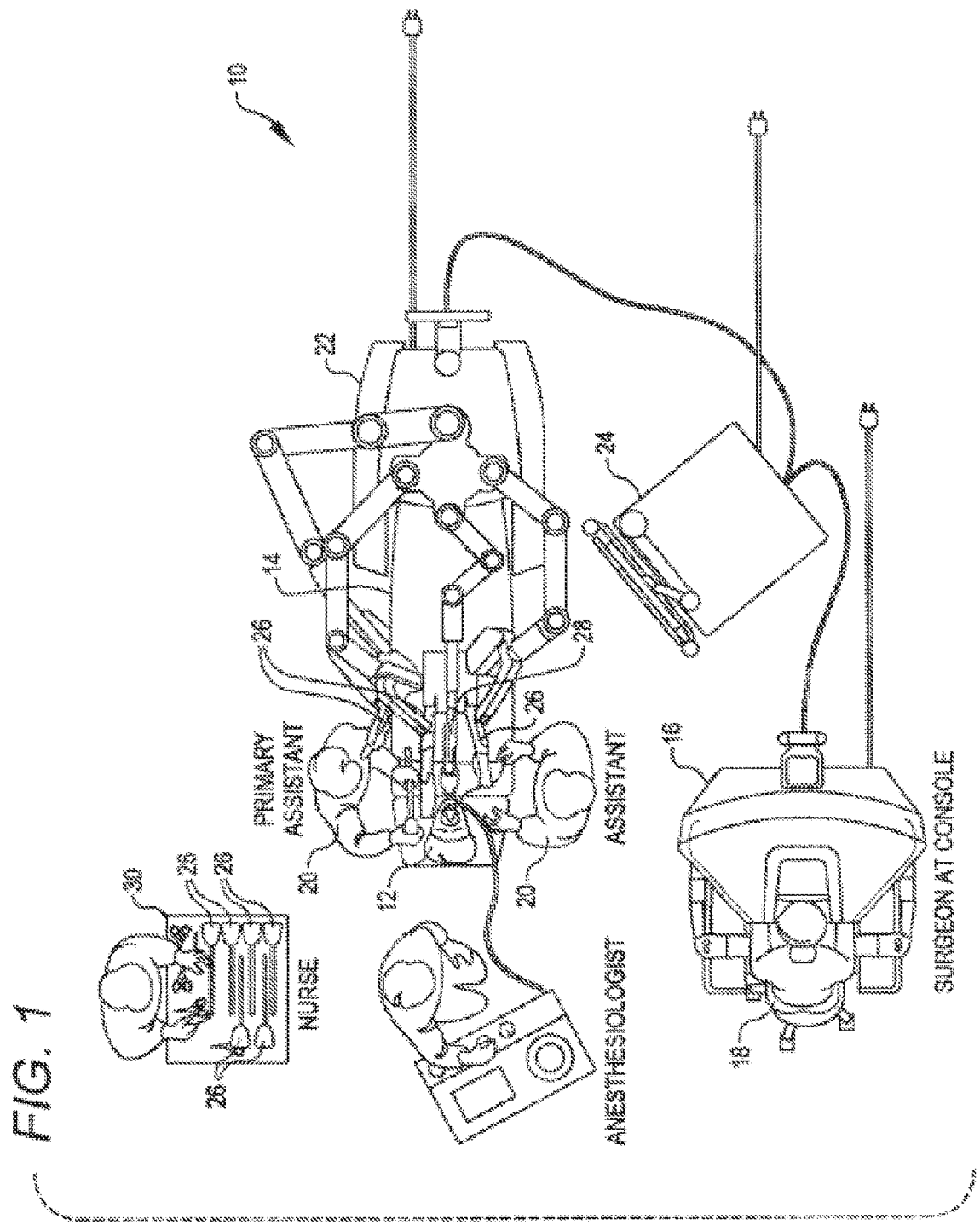
FIG. 1 is a plan view of a minimally invasive robotic surgery system being used to perform a surgery, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The kinematic linkage structures and control systems described herein are particularly beneficial in helping system users to arrange the robotic structure of a procedure on a particular patient. The damping of these kinematic linkage structures can increase the control a surgeon has over movement of one or several surgical tools, and thus can allow a more precise surgery. In this description, actively driven, active, or forward-driven means a motor assists motion of a joint, and passive means a joint must be moved in some way from outside the system. Some actively driven joints are teleoperated, such as joints in a teleoperated surgical instrument manipulator under a surgeon's control. Other forward-driven driven joints are not teleoperated, such as joints operated by a switch near the joint or that are associated with an automatic function such as compensating for gravity effects on a kinematic chain to make the end of the chain appear weightless at various changing poses. Along with forward-driven manipulators used to interact with tissues and the like during treatment, robotic surgical systems may have one or more kinematic linkage systems that are configured to support and help align the manipulator structure with the surgical work site. These set-up systems may be forward-driven or may be passive, so that they are manually articulated and then locked into the desired configuration while the manipulator is used therapeutically and/or operatively. The passive set-up kinematic systems may have advantages in size, weight, complexity, and cost. However, a plurality of manipulators may be used to treat tissues of each patient, and the manipulators may each independently benefit from accurate positioning so as to allow the instrument supported by that instrument to have the desired motion throughout the workspace. Minor changes in the relative locations of adjacent manipulators may have significant impact on the interactions between manipulators (for example, they may collide with each other, or the rigidity of the kinematics of the pose may be low enough to result in large structural vibrations). Hence, the challenges of optimally arranging the robotic system in preparation for surgery can be significant.

One option is to mount multiple manipulators to a single platform, with the manipulator-supporting platform sometimes being referred to as an orienting platform. The orienting platform can be supported by a forward-driven support linkage (sometimes referred to herein as a set-up structure, and typically having a set-up structure linkage, etc.) The system may also provide and control motorized axes of the robotic set-up structure supporting the orienting platform with some kind of joystick or set of buttons that would allow the user to forward-drive those axes as desired in an independent fashion. This approach, while useful in some situations, may suffer from some disadvantages. Firstly, users not sufficiently familiar with robotics, kinematics, range of motion limitations and manipulator-to-manipulator collisions may find it difficult to know where to position the orienting platform in order to achieve a good setup. Secondly, the presence of any passive joints within the system means that the positioning of the device involves a combination of manual adjustment (moving the passive degrees of freedom by hand) as well as controlling the active degrees of freedom, which can be a difficult and time-consuming iterative activity.

To maintain the advantages of both manual and forward-driven positioning of the robotic manipulators, embodiments of the robotic systems described herein may employ a set-up mode in which one or more joints are forward-driven in response to manual articulation of one or more other joints of the kinematic chain. In many embodiments, the forward-driven joints will move a platform-supporting linkage structure that supports multiple manipulators, greatly facilitating the arrangement of the overall system by moving those manipulators as a unit into an initial orientational and/or positional alignment with the workspace. Independent positioning of one, some or all of the manipulators supported by the platform can optionally be provided through passive set-up joint systems supporting one, some, or all of the manipulators relative to the platform.

Minimally Invasive Robotic Surgery

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (a teleoperated surgical system that employs robotic technology—a surgical robot) and an Auxiliary Equipment Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Equipment Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
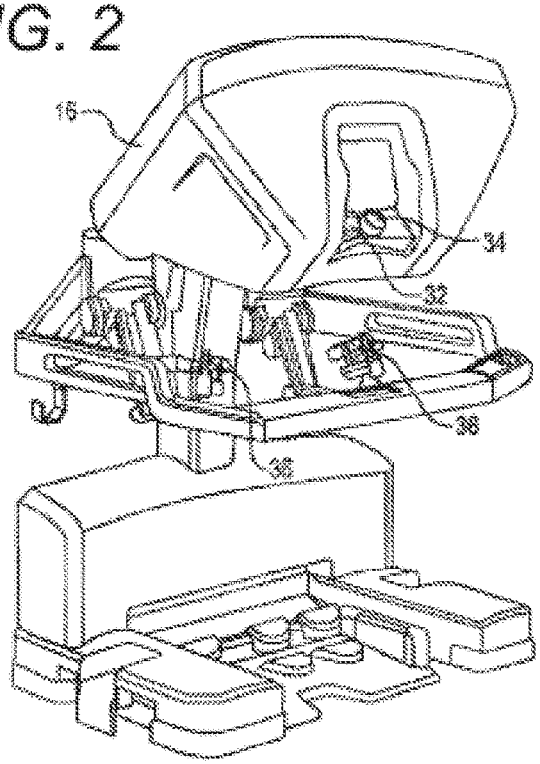
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
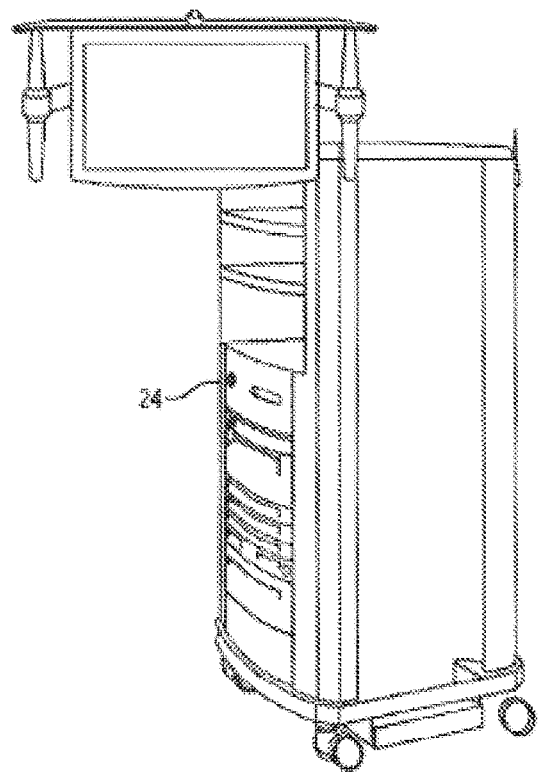
FIG. 3 is a perspective view of a robotic surgery system electronics cart, in accordance with many embodiments.

FIG. 3 is a perspective view of the Auxiliary Equipment Cart 24. The Equipment Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Equipment Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Equipment cart 24 may include other surgical system components, such as at least part of a computer control system used to control the system, endoscopic illumination equipment, electrosurgery equipment, and other medically-related devices.

Figure 4:
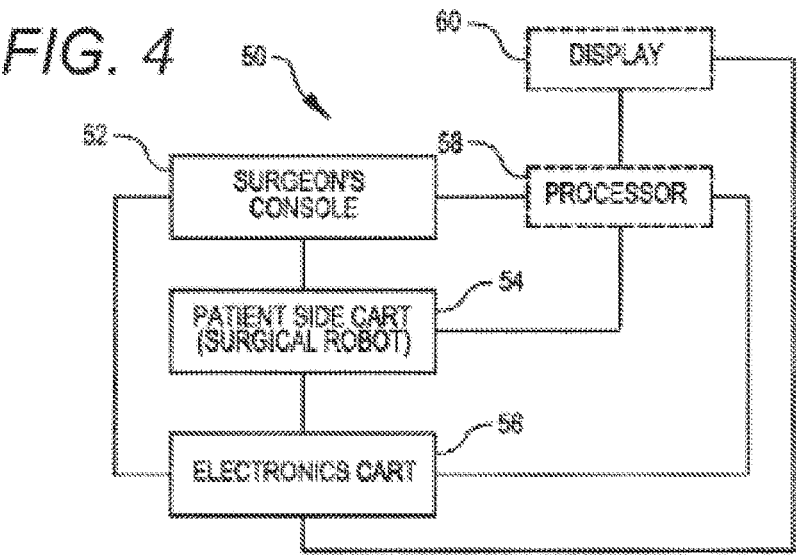
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Equipment Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Processor 58 will typically include a combination of hardware and software, with the software comprising tangible media embodying computer readable code instructions for performing the method steps of the control functionally described herein. The hardware typically includes one or more data processing boards, which may be co-located but will often have components distributed among the robotic structures described herein. The software will often comprise a non-volatile media, and could also comprise a monolithic code but will more typically comprise a number of subroutines, optionally running in any of a wide variety of distributed data processing architectures.

Figure 5A:
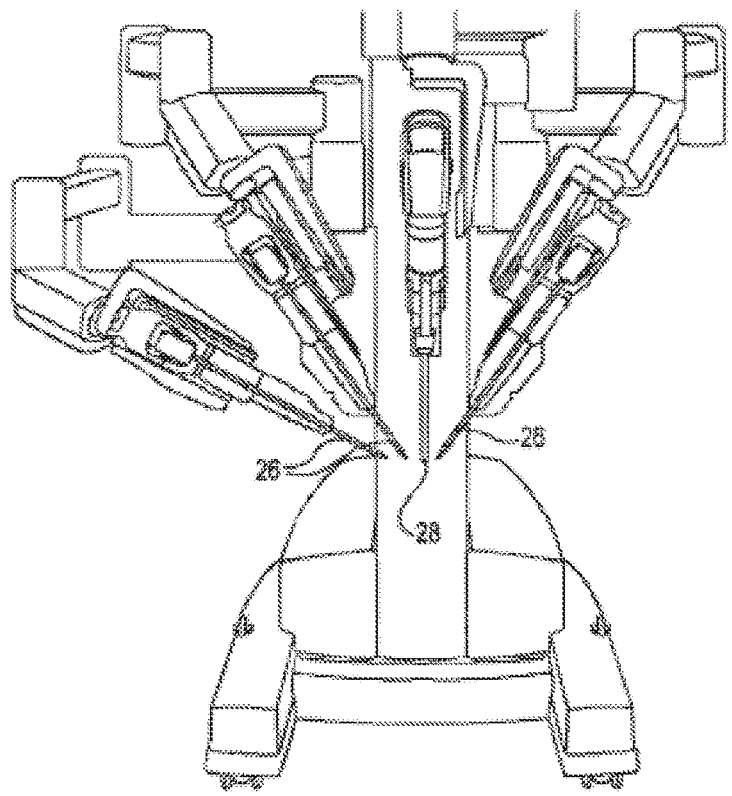
FIG. 5A is a partial view of a patient side cart (surgical robot) of a robotic surgery system, in accordance with many embodiments.
Figure 5B:
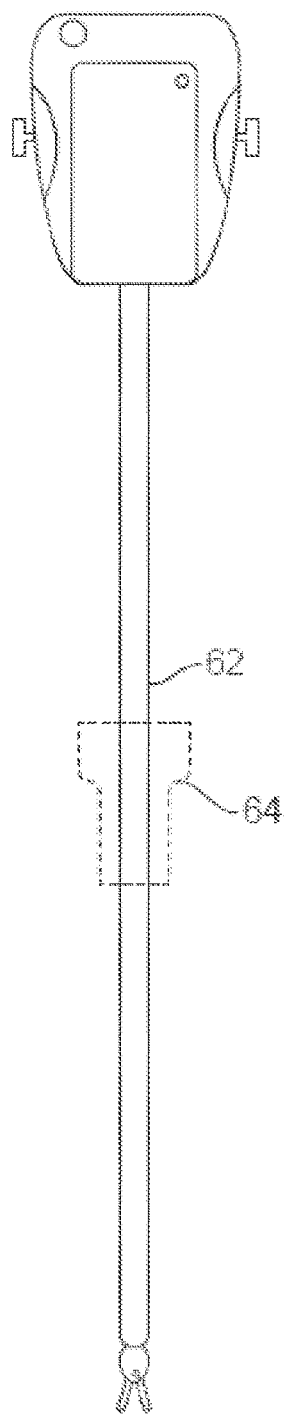
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical tools 26 are inserted into the patient by inserting a tubular cannula 64 through a minimally invasive access aperture such as an incision, natural orifice, percutaneous penetration, or the like. Cannula 64 is mounted to the robotic manipulator arm and the shaft of surgical tool 26 passes through the lumen of the cannula. The manipulator arm may transmit signals indicating that the cannula has been mounted thereon.

Robotic Surgery Systems and Modular Manipulator Supports

Figure 6:
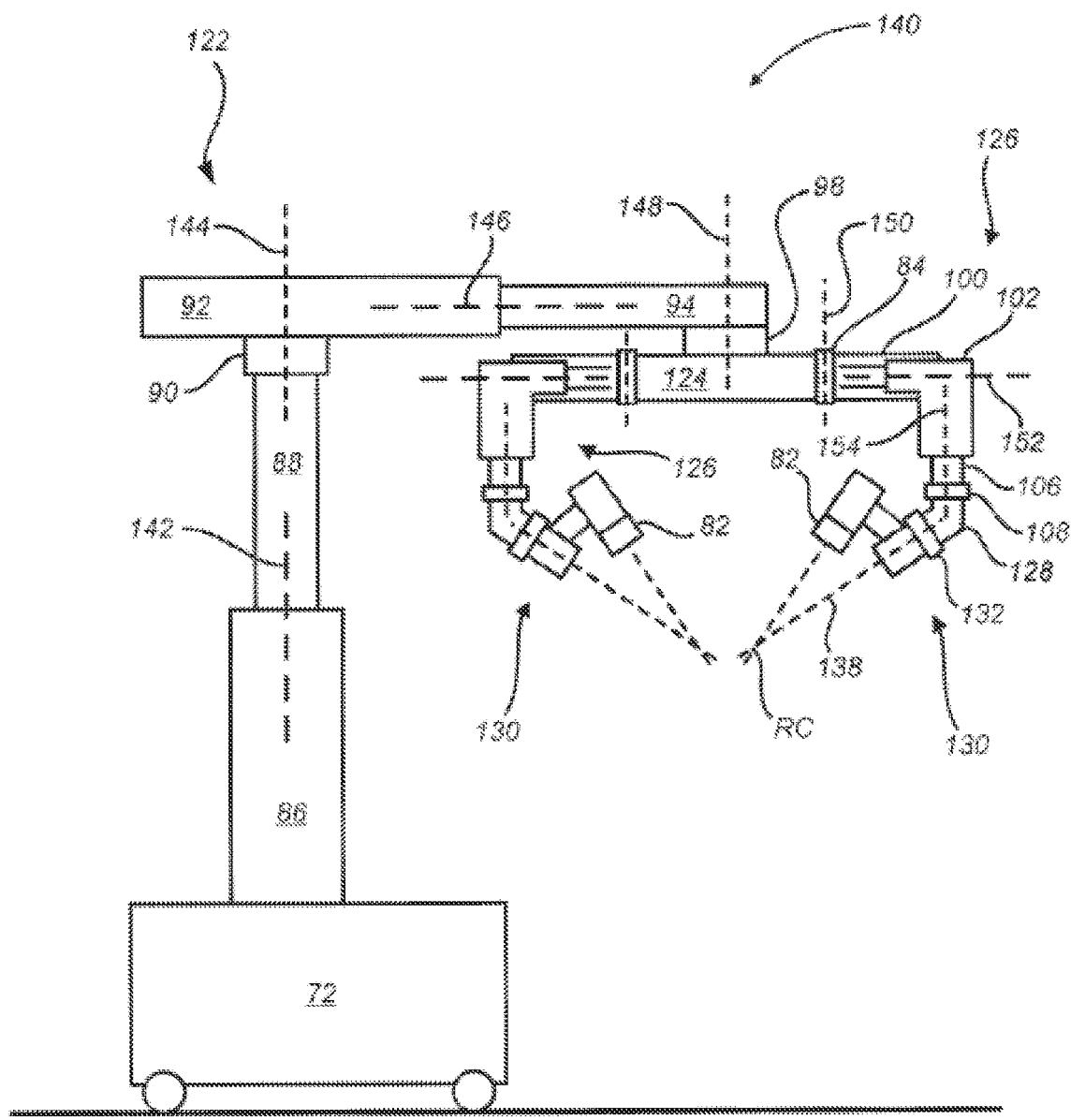
FIG. 6 shows a robotic surgery system, in accordance with many embodiments.

FIG. 6 is a simplified representation of a robotic surgery system 140, in accordance with many embodiments. The robotic surgery system 140 includes a mounting base 72, alternatively referred to herein as a base, a support linkage 122, an orienting platform 124, a plurality of set-up linkages 126 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by a first set-up linkage joint 84. Each of the set-up linkages 126 is fixedly attached to and supported by the orienting platform 124. The orienting platform 124 is rotationally coupled to and supported by the support linkage 122. And the support linkage 122 is fixedly attached to and supported by the mounting base 72.

In many embodiments, the mounting base 72 is a movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have other suitable configurations, for example, a ceiling mount, fixed floor/pedestal mount, a wall mount, or an interface configured for being supported by any other suitable mounting surface.

The support linkage 122 is configured to selectively position and orient the orienting platform 124 relative to the mounting base 72 via relative movement between links of the support linkage 122 along multiple set-up structure axes. The support linkage 122 includes a column base 86, a translatable column member 88, a shoulder joint 90, a boom base member 92, a boom first stage member 94, and a wrist joint 98. The column base 86 is fixedly attached to the mounting base 72. The translatable column member 88 is selectively repositionable relative to the column base 86 along a first set-up structure (SUS) axis 142, which is vertically oriented in many embodiments. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. Accordingly, the support linkage 122 is operable to selectively set the distance between the shoulder joint 90 and the distal end of the boom first stage member 94. And the wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the mechanism support link 128 relative to the set-up linkage vertical link 106 around the third SUJ axis 154. Each of the joints 132 is operable to rotate the associated manipulator 82 around the associated axis 138.

Figure 7:
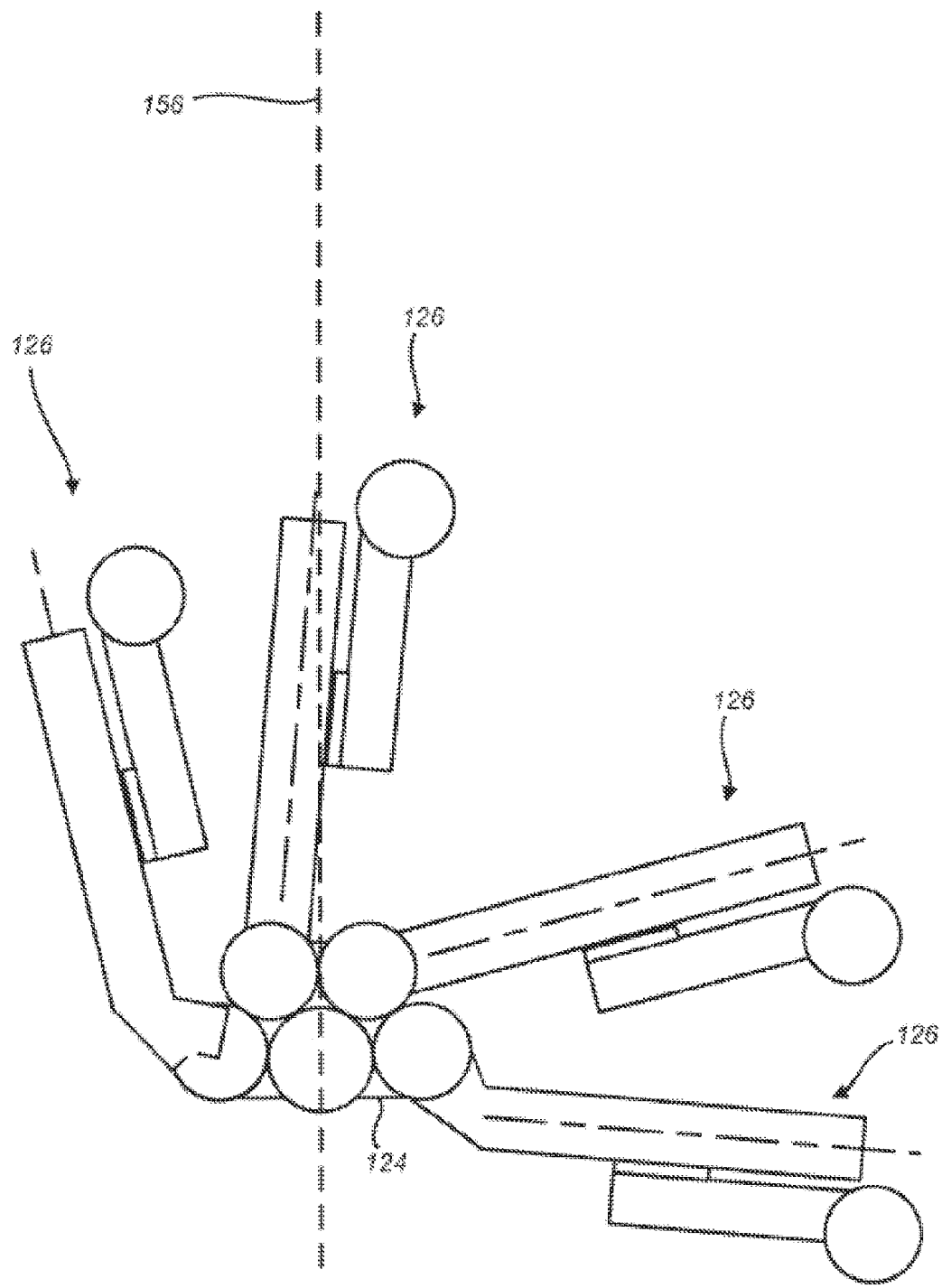
FIG. 7 illustrates rotational orientation limits of set-up linkages relative to an orienting platform of the robotic surgery system of FIG. 6.

FIG. 7 illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 7 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction.

Figure 8:
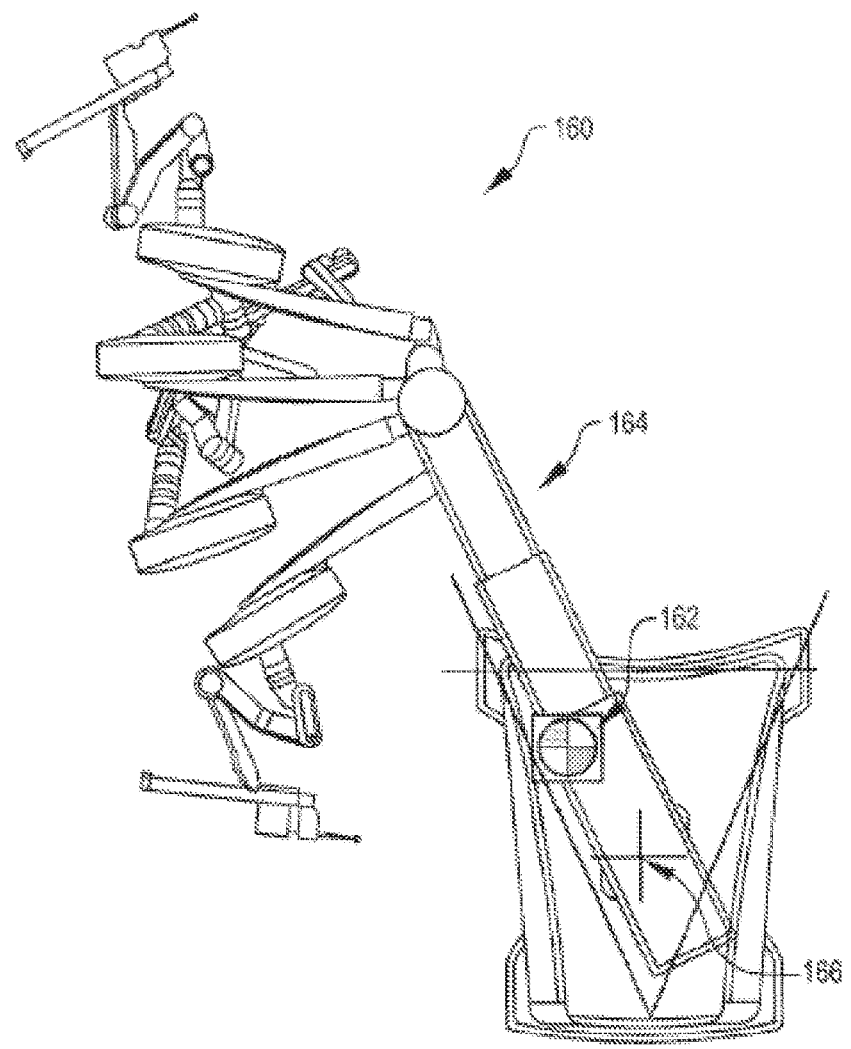
FIG. 8 shows a center of gravity diagram associated with a rotational limit of the boom assembly for a robotic surgery system, in accordance with many embodiments.

FIG. 8 shows a center of gravity diagram associated with a rotational limit of a support linkage for a robotic surgery system 160, in accordance with many embodiments. With components of the robotic surgery system 160 positioned and oriented to shift the center-of-gravity 162 of the robotic surgery system 160 to a maximum extent to one side relative to a support linkage 164 of the surgery system 160, a shoulder joint of the support linkage 164 can be configured to limit rotation of the support structure 164 around a set-up structure (SUS) shoulder-joint axis 166 to prevent exceeding a predetermined stability limit of the mounting base.

Figure 9:
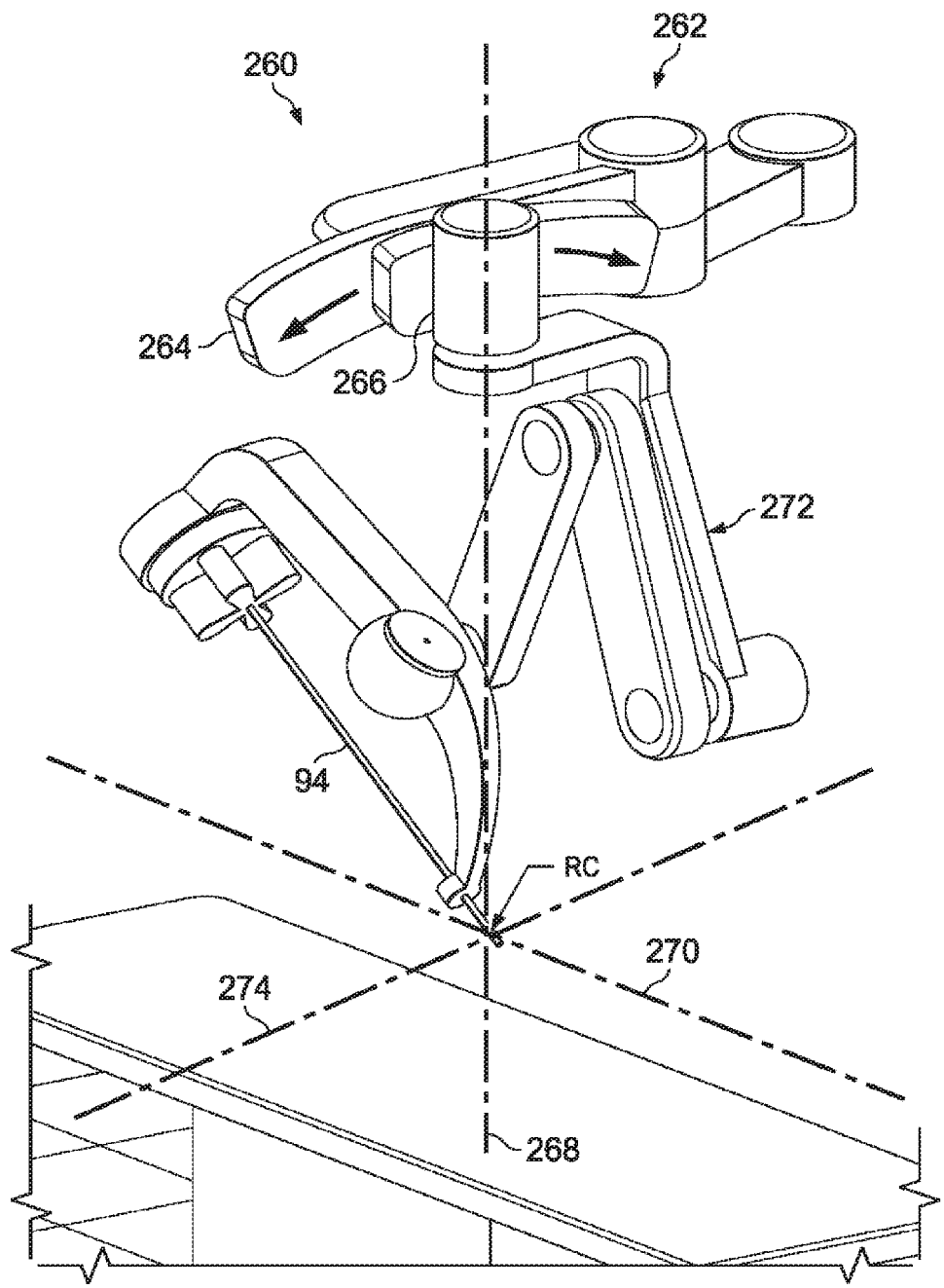
FIG. 9 shows a remote center manipulator, in accordance with many embodiments, that includes a curved feature having a constant radius of curvature relative to the remote center of manipulation and along which a base link of the outboard linkage can be repositioned.

FIG. 9 illustrates another approach for the implementation of a redundant axis that passes through the remote center of manipulation (RC) and the associated redundant mechanical degree of freedom. FIG. 9 shows a remote center manipulator 260, in accordance with many embodiments, that includes a mounting base 262 that includes a curved feature 264 having a constant radius of curvature relative to the remote center of manipulation (RC) and along which a base link 266 of the outboard (proximal) linkage of the manipulator 260 can be repositioned. The outboard linkage is mounted to the base link 266, which includes a "yaw" joint feature, for rotation about a first axis 268 that intersects the remote center of manipulation (RC). The base link 266 is interfaced with the curved feature 264 such that the base link 266 is constrained to be selectively repositioned along the curved feature 264, thereby maintaining the position of the remote center of manipulation (RC) relative to the mounting base 262, which is held in a fixed position relative to the patient. The curved feature 264 is configured such that movement of the base link 266 is limited to rotation about a second axis 270 that intersects the remote center of manipulation (RC). By changing the position of the base link 266 along the curved feature 264, the orientation of the outboard linkage of the manipulator 260 relative to the patient can be varied, thereby providing for increased range of motion of the surgical instrument manipulated by the remote center manipulator 260. Parallelogram mechanism 272 provides rotation around axis 274. It can be seen that as the entire parallelogram mechanism rotates around axis 268, axes 270 and 274 can be made coincident.

Figure 10:
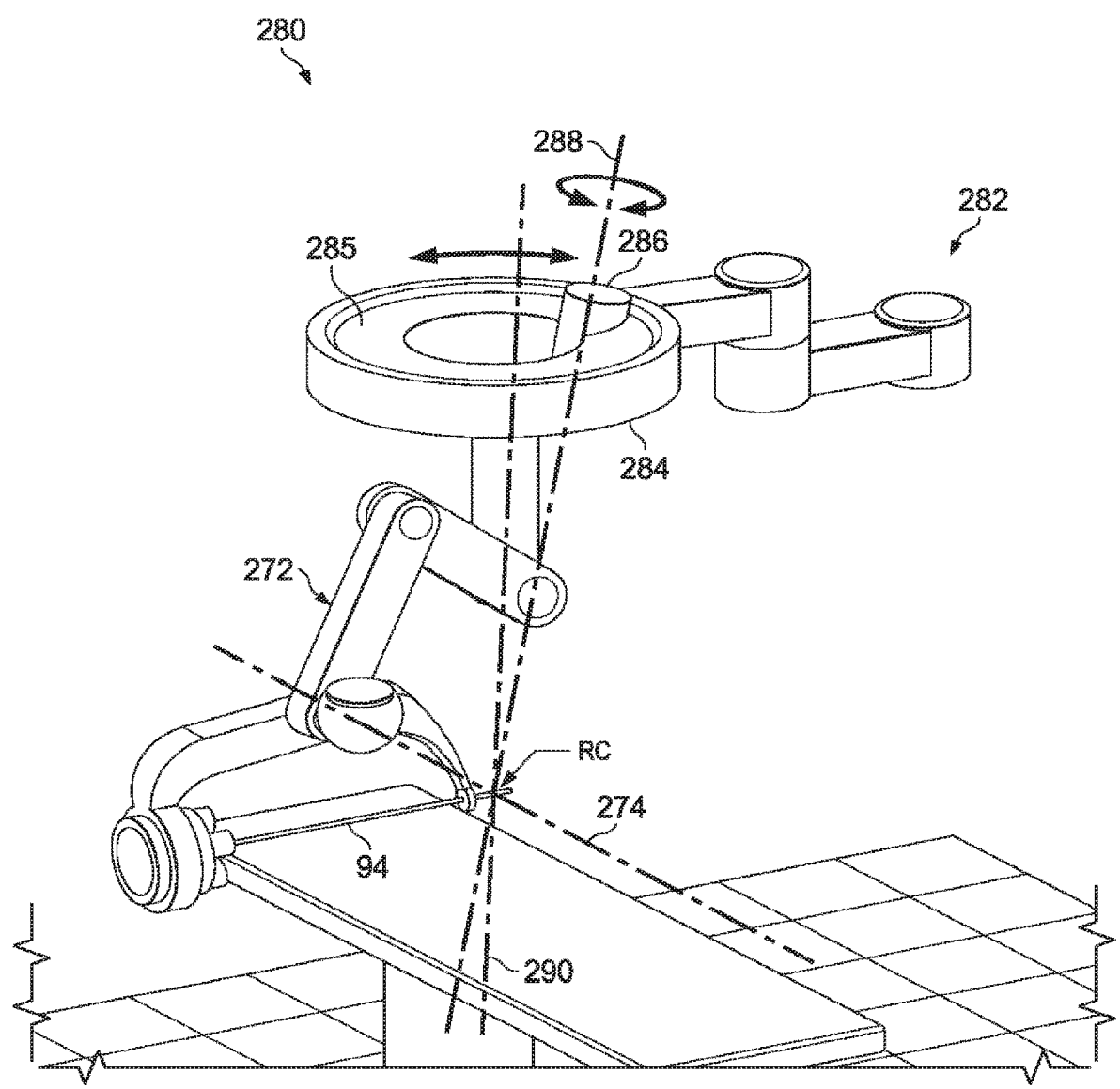
FIG. 10 shows a remote center manipulator, in accordance with many embodiments, that includes a closed-loop curved feature to which a base link of the outboard linkage is interfaced such that the base link is constrained to move along the closed-loop curved feature.

FIG. 10 illustrates another approach for the implementation of a redundant axis that passes through the remote center of manipulation (RC), providing an associated redundant degree of freedom. FIG. 10 shows a remote center manipulator 280, in accordance with many embodiments, that includes a mounting base 282 that includes a closed-loop curved feature 284 inside which a base link 286 of the outboard (distal) linkage of the manipulator 280 can be repositioned. As shown, central mount element 285 rotates inside closed-loop curved feature 284. Base link 286 is mounted on the central mount element 285 to be oriented somewhat inward toward the remote center of manipulation. The outboard linkage is mounted to the base link 286 for rotation about a first axis 288 that intersects the remote center of manipulation (RC). The closed-loop curved feature 284 is configured such that, for all positions of the base link 286 around the curved feature 284, the position of the remote center of manipulation (RC) remains fixed relative to the mounting base 282, which is held fixed relative to the patient. The closed-loop curved feature 284 is circular and is axially-symmetric about a second axis 290 that intersects the remote center of manipulation (RC). By changing the position of the base link 286 around the closed-loop curved feature 284, the orientation of the outboard linkage of the manipulator 280 relative to the patient can be varied, thereby providing for increased range of motion, arm-to-arm or arm-to-environment collision avoidance, and/or kinematic singularity avoidance for the remote center manipulator 280. A "partial circle" feature or a full circular feature where the mounting base only traverses a portion of the circle can also be used. It can be seen that curved feature 284 and its associated central mount feature 285 act as a conical sweep joint.

Figure 11:
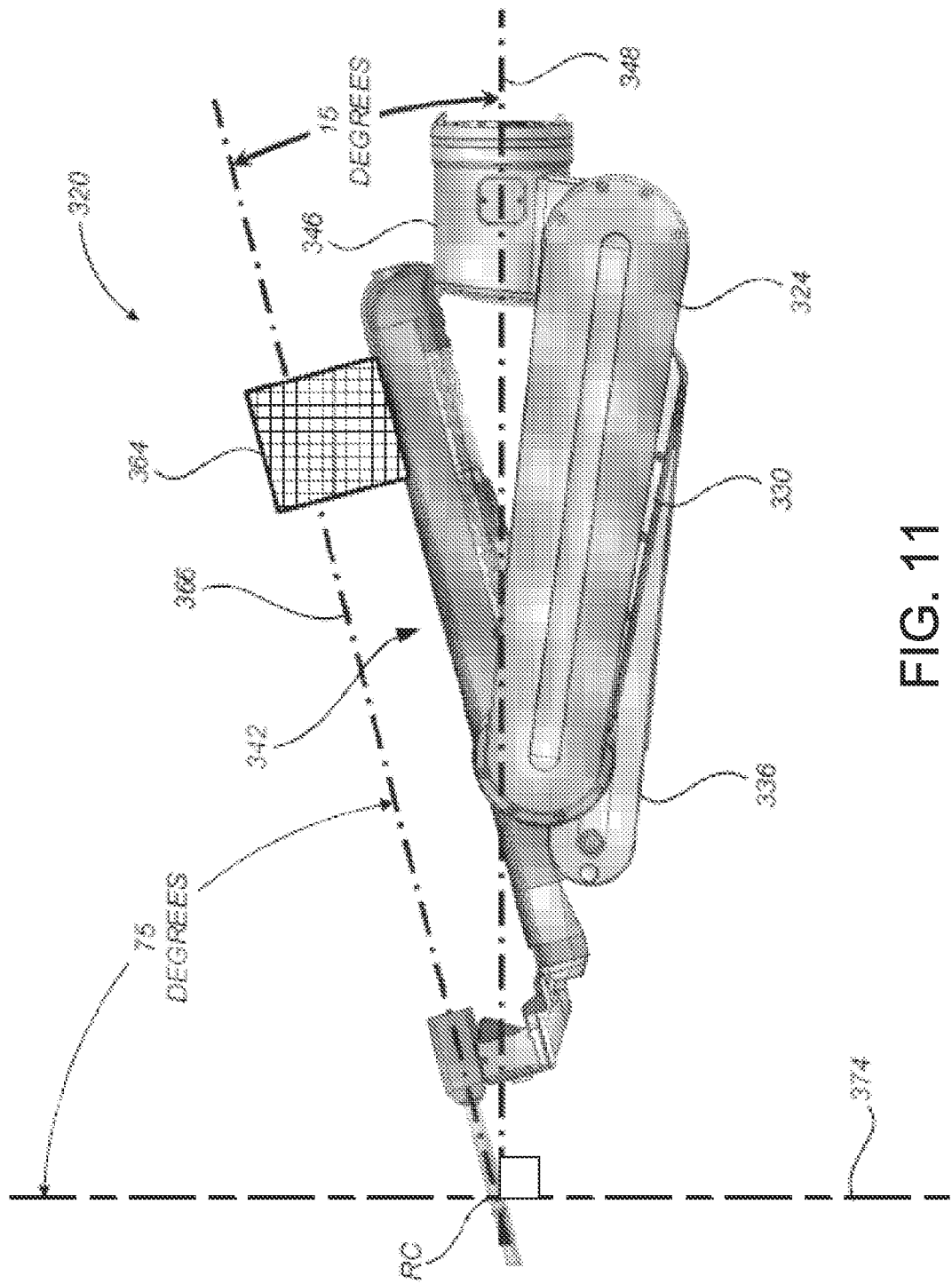
FIG. 11 is a side view of the remote center manipulator in a configuration of maximum pitch back of the instrument holder relative to the remote center of manipulation, in accordance with many embodiments.

FIG. 11 is a side view of the remote center manipulator 320 in which the instrument holder 342, which can, for example, hold a surgical instrument, is pitched back to a maximum amount. In the configuration shown, the first parallelogram link 330 has been swung to a position just past being aligned with the extension link 324 and the second parallelogram link 336 has been swung to a position just past being aligned with the first parallelogram link 330, thereby orienting the insertion axis 366 to an angular offset of 75 degrees from a perpendicular 374 to the yaw axis 348. While the remote center manipulator 320 can be configured to achieve even greater maximum pitch back angle, for example, by increasing the length of the extension link 324 such that the instrument holder 342 does not come into contact with the yaw/pitch housing 346, the additional pitch back angle gained may not be of practical value given that the kinematics of the remote center manipulator 320 with regard to yawing of the instrument holder 342 relative to the remote center of manipulation (RC) becomes increasingly poorly conditioned when the angle between the insertion axis 366 and the yaw axis 348 is reduced below 15 degrees.

Figure 12:
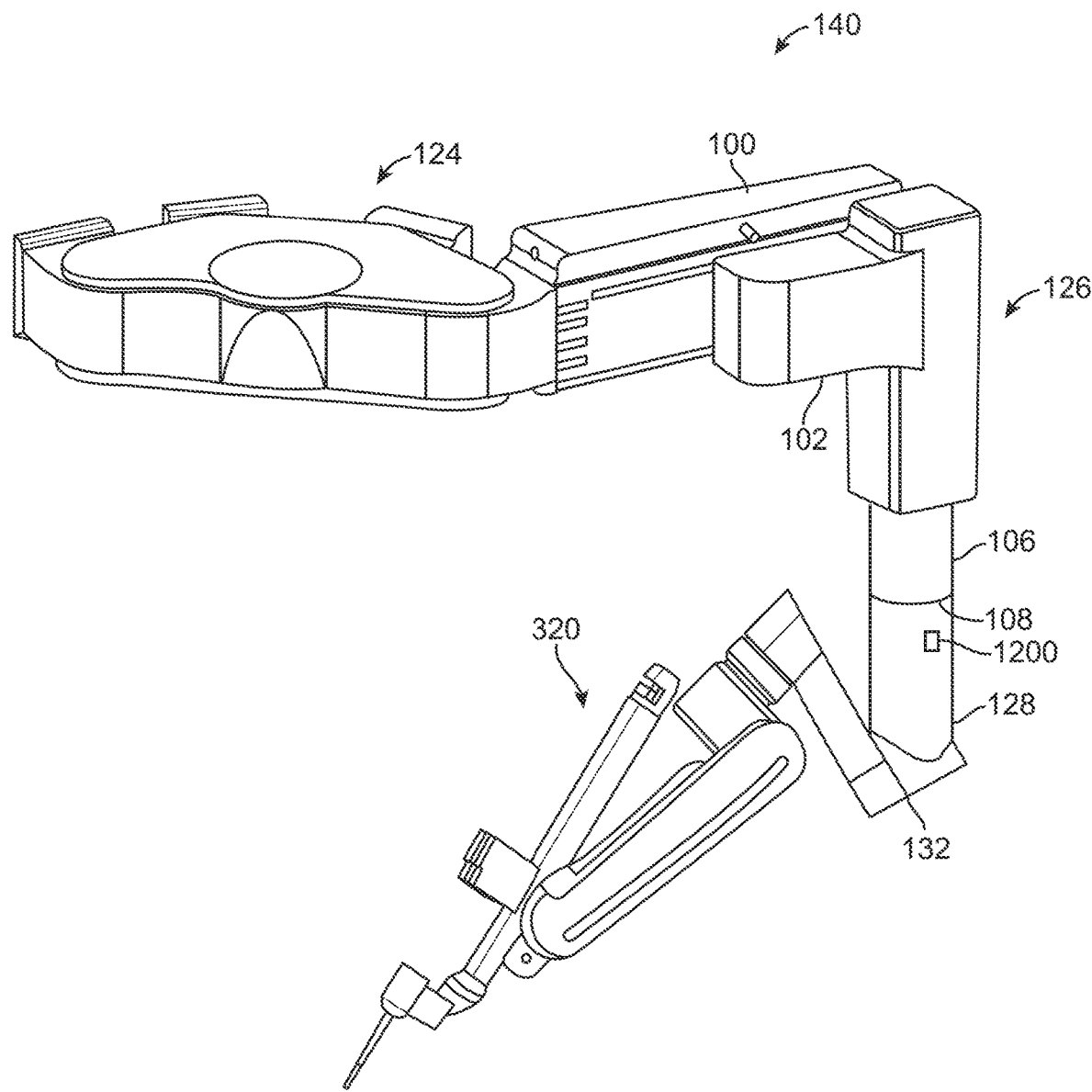
FIG. 12 is a perspective view of one embodiment of a portion of the robotic surgery system.

FIG. 12 is a perspective view of one embodiment of a portion of the robotic surgery system 140. The robotic surgery system 140 depicted in FIG. 12 includes the orienting platform 124 with a single set-up linkage 126 attached to the orienting platform, although, in some embodiments, multiple set-up linkages 126 can connect to the orienting platform. The set-up linkage 126 includes the set-up linkage base link 100 connected to the orienting platform 124. As seen in FIG. 12, the set-up link extension link 102 slidably connects to the set-up link base link 100. Extending vertically from the set-up link extension link 102 is the set-up linkage vertical link 106 that rotatably connects to the support link 128 via set-up linkage second joint 108. The distal end, with respect to the orienting platform 124, of the support link 128 is connected via joint 132 to the remote center manipulator 320.

In some embodiments, the robotic surgery system 140 can include one or several sensors 1200 that can be located at a variety of different positions on the robotic surgery system 140. In some embodiments, the sensors 1200 can be located on one or several of the linkages of the robotic surgery system 140, and in some embodiments, the sensors 1200 can be located on the remote center manipulator 320. In one particular embodiment, the sensors 1200 can be located on the portion of the remote center manipulator 320 proximate to the surgical tool.

The sensors 1200 can comprise any desired sensor, and in some embodiments, the sensors 1200 can be configured to sense a position, a velocity, an acceleration, a jerk, a vibration, and/or the like. In one embodiment, the sensors 1200 can comprise at least one accelerometer that can be located at a distal end of the remote center manipulator 320 and/or at a distal end of the set-up linkage 126.

Damping of Robotic Surgery Systems

In some embodiments, MIRS 10 can be passively, actively, and/or semi-actively damped. In some embodiments, some or all of the set-up linkages 126 of MIRS 10 are damped such that vibrations arising in one of the set-up linkages 126 are mitigated to minimize vibration, and the therewith associated motion, in that set-up linkage 126. Additionally, in some embodiments, a vibration arising in one or more of the set-up linkages 126 may travel from the source of the vibration in the one or more set-up linkages 126 to others of the set-up linkages 126. This can result in a vibration arising in one or more of the set-up linkages 126 causing a vibration in some or all of the other set-up linkages, which can degrade the performance of MIRS 10.

In one embodiment, the set-up linkages can be vibrationally isolated from each other by one or several dampers. These one or several dampers can minimize vibration in a set-up linkage 126, which vibration arises in another set-up linkage 126. In some embodiments, these one or several dampers can be passive, and in some embodiments, these one or several dampers can be semi-active and/or active. In some embodiments, one or several sensors on one set-up linkage 126 can measure a locally experienced vibration arising due to a motion, acceleration, or vibration of another set-up linkage 126, and can use this data to damp the locally experienced vibration.

Figure 13:
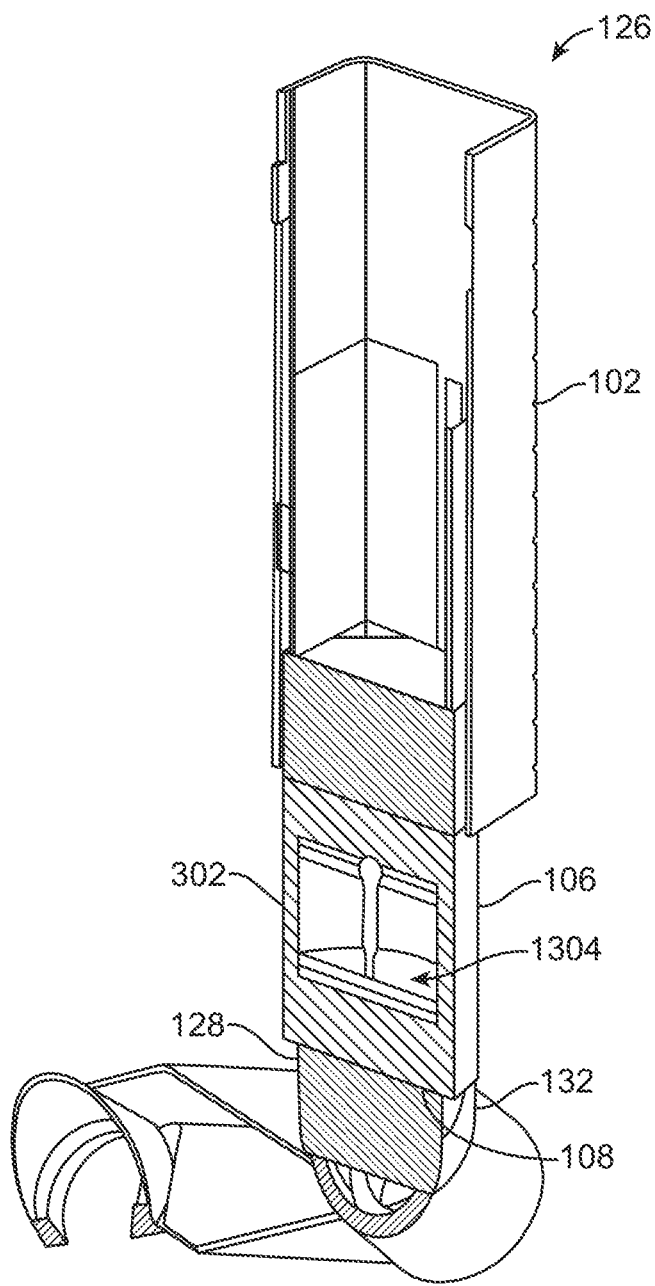
FIG. 13 is a section view of one embodiment of portions of the set-up linkage.

FIG. 13 is a section view of one embodiment of portions of the set-up linkage 126 shown in FIG. 12. As seen in FIG. 13, the set-up linkage vertical link 106 has an exemplary internal volume 1302. In some embodiments, the internal volume 1302 of the set-up linkage vertical link 106 can comprise a variety of shapes and sizes. In the embodiment depicted in FIG. 13, the internal volume 1302 contains a damper 1304 that can be attached at one end to the set-up linkage vertical link 106 and at the other end to the support link 128. Although the damper 1304 is depicted in the internal volume 1302 of the set-up linkage vertical link 106, the damper 1304 can be placed in any other desired location in which it can effectively damp vibrations occurring in the set-up linkage 126 or in MIRS 10. In some embodiments, the damper 1304 can be located at a distal end of the set-up linkage 126, at a distal end of the remote center manipulator 320, and/or at any other position.

Damper 1304 can comprise a variety of shapes, sizes, and designs. The damper 1304 can comprise an active damper, a semi-active damper, and/or a passive damper. In some embodiments, an active damper can be used to actively damp one or several vibrations. This can include, for example, generating one or several forces, acceleration, and/or motions that cancel and/or mitigate a vibration. In some embodiments, this can further include input shaping to control the motion of a portion of MIRS 10 to minimize created vibrations. In some embodiments, a semi-active damper can be used to semi-actively damp one or several vibrations. In some embodiments, a semi-active damper can include one or several features that are adjustable to affect the damping coefficient of the semi-active damper based on one or several measured and/or expected vibrations. In some embodiments, a passive damper can be used to passively damp one or several vibrations. The passive damper can maintain a constant damping coefficient.

In some embodiments, damper 1304 can be made from a variety of materials and/or components. In some embodiments, damper 1304 can be configured to damp any desired number of degrees of freedom (DOF). In one embodiment, for example, the damper 1304 can be configured to damp 1 DOF, 2 DOF, 3 DOF, 4 DOF, 5 DOF, 6 DOF, or any other number or combination of DOFs.

The damper 1304 can be configured to provide any desired damping, including, for example, passive damping or variable damping which can include one or both of active damping and semi-active damping. In some embodiments, the desired damping can be selected based on the desired frequency and magnitude of expected and/or measured vibrations to be damped. Different example embodiments of the damper 1304 are depicted in FIGS. 14-18, and are identified as dampers 1400, 1500, 1600, 1700, and 1800.

In one embodiment, the damper 1304 can comprise one or several voice coils, also referred to herein as one or several voice coil linear motors. In some embodiments, the one or several voice coils can be located at any desired position on the set-up linkage 126 and/or on the remote center manipulator 320. In one embodiment, the one or several voice coils can each be placed where a force giving rise to a vibration occurs, and positioned so as to be able to counteract the force giving rise to the vibration to thereby dissipate and/or eliminate the vibration. In one embodiment, this can result in the placement of one or several of the voice coils at different locations on the robotic surgical system 140 and in different positions and/or orientations with respect to the robotic surgical system 140. In one embodiment, a combination of voice coils may be used to damp vibrations occurring along 1, 2, and/or 3 axes.

Figure 14:
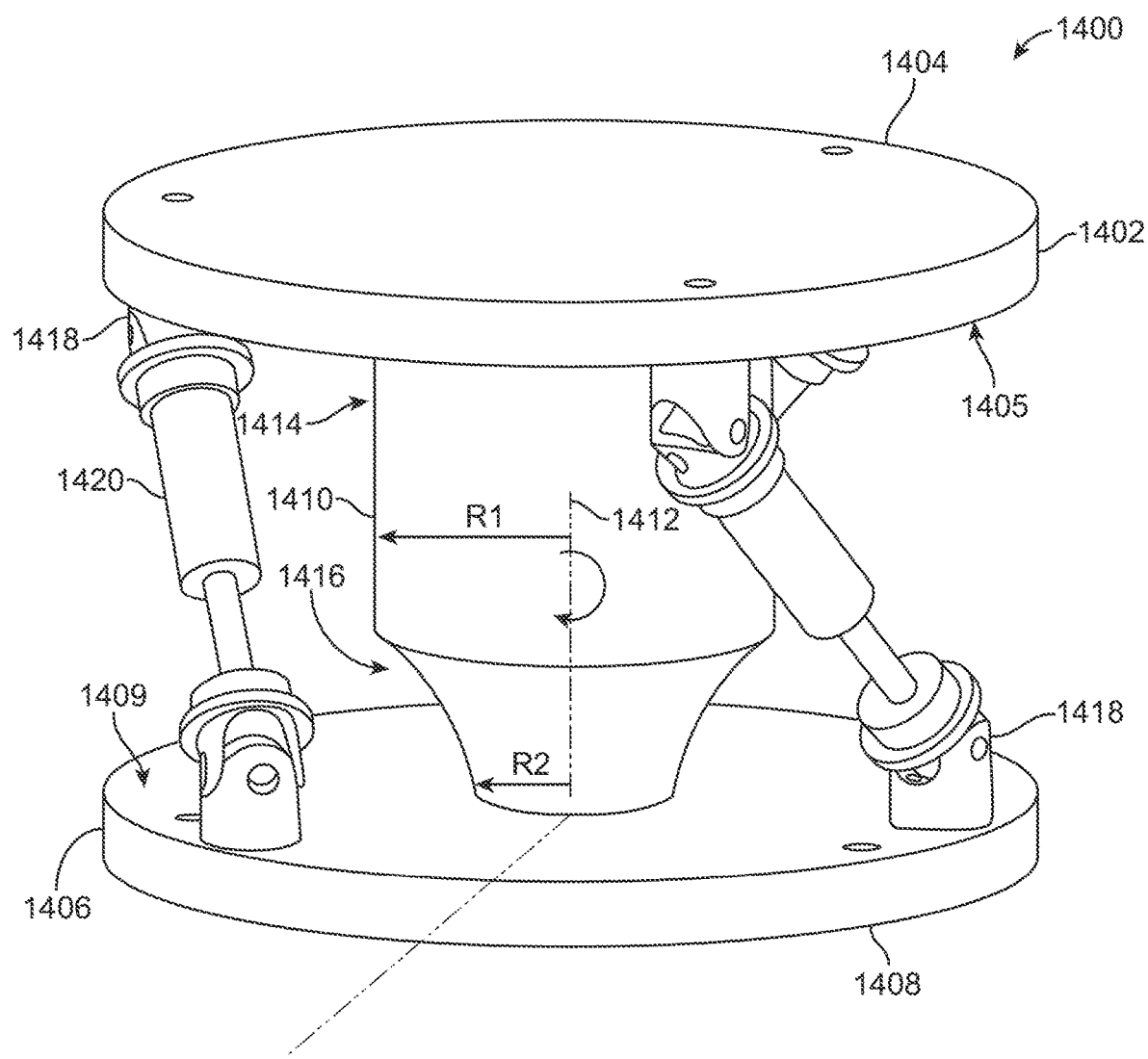
FIG. 14 is a perspective view of one embodiment of a damper for use with the robotic surgery system.

FIG. 14 is a perspective view of one example embodiment of a damper 1400. The damper 1400 comprises a damping platform that can be a 3 DOF damping platform. The damper 1400 has a top plate 1402 having a top surface 1404 and a bottom surface 1405 opposite the top surface 1404, and a bottom plate 1406 having a bottom surface 1408 and a top surface 1409 opposite the bottom surface 1406. In the embodiment depicted in FIG. 14, both the top plate 1402 and the bottom plate 1406 comprise cylindrical members, but in some embodiments, these plates 1402, 1406 can comprise any other desired shape or form. The plates 1402, 1406 can be made of a variety of materials. In some embodiments, the plates 1402, 1406 can be made from a rigid material and in some embodiments, the plates 1402, 1406 can be made from a flexible material.

In some embodiments, and as depicted in FIG. 13, the top plate 1402 and the bottom plate 1406 can be configured to mate with and/or mechanically connect with portions of the set-up linkage 126. In one particular embodiment, the top plate 1402, and specifically the top surface 1404 of the top plate 1402 can connect to a portion of the set-up linkage vertical link 106 and the bottom plate 1406, and particularly the bottom surface 1408 of the bottom plate 1406 can connect to the support link 128.

The top plate 1402 and the bottom plate 1406 are connected by a flexure, and specifically by a torsional/bending flexure 1410. The torsional/bending flexure 1410 can be connected to any portion of one or both of the plates 1402, 1406. In the embodiment depicted in FIG. 14, the torsional/bending flexure 1410 is connected to the center of the bottom surface 1405 of the top plate 1402 and to the center of the top surface 1409 of the bottom plate 1406. This connection to the center of the plates 1402, 1406 is indicated by axis 1412 that extends through the torsional/bending flexure 1410 and through the plates 1402, 1406.

The torsional/bending flexure 1410 can comprise a variety of shapes and sizes. In some example embodiments, the torsional/bending flexure 1410 can comprise a cylindrical member, a triangular prism, a rectangular prism, a pentagonal prism, a hexagonal prism, or any other desired shape or combination of shapes. In the embodiment depicted in FIG. 14, the axial member comprises a first portion 1414 nearest the top plate 1402 and a second portion 1416 nearest the bottom plate 1406. In the embodiment of FIG. 14, the first portion 1414 comprises a cylinder having a radius R1 and the second portion 1416 comprises the top half of a hyperboloid of one sheet.

The torsional/bending flexure 1410 can be made from a variety of materials. In some embodiments, the torsional/bending flexure 1410 can comprise a material that is elastically deformable over the range of forces from the robotic surgery system 140. In some embodiments, this elastic deformation results in the generation of a restorative force, which can move the flexure 1410 to an undeflected position after the applied force terminates. In some embodiments, the torsional/bending flexure 1410 can comprise an elastomeric material, rubber, metal including, for example, steel, aluminum, titanium, or the like, or any other elastic material.

In some embodiments, the damper 1400 can comprise one or several mounts 1418 that can be located on one or both of the plates 1402, 1406. In the embodiment depicted in FIG. 14, the damper 1400 comprises three mounts 1418 located on, and arranged around the perimeter of, the bottom surface 1405 of the top plate 1402 and three mounts 1418 located on, and arranged around the perimeter of, the top surface 1409 of the bottom plate 1406. The mounts 1418 can connect one or several damping units 1420, also referred to herein as damping elements, to one or both of the plates 1402, 1406. In some embodiments, the mounts 1418 can comprise a 3-DOF mounts including, for example, 3-DOF ball joint mounts. In one embodiment, the mounts 1418 can comprise a 2-DOF U-joint mounted on a 1-DOF rotary base. In one embodiment, the 1-DOF rotary base can be mounted to rotate about an axis parallel to axis 1412 shown in FIG. 14. The damping units 1420 can comprise any features that, in connection with the damper 1400, damp vibrations arising from movement of the set-up linkage 126. In some embodiments, the damping units 1420 can be a passive damping unit that is not controllable to alter its damping coefficient. In some embodiments, the damping units 1420 can be one or several variable damping units which can actively and/or semi-actively damp vibrations, also referred to herein as dynamic damping units. In some embodiments, the variable damping unit can be controllable and/or include one or several variable components that can be controllable, to alter the damping coefficient of the variable damping unit. These variable damping units can include a variable hydraulic shock absorber, a variable magnetic shock absorber, a variable pneumatic shock absorber, or any other kind of variable shock absorber. In some embodiments, an variable damping unit can include, for example, a variable component such as one or several actuators that can be used to move all or portions of the damper and/or to generate one or several forces or accelerations in all or portions of MIRS 10, to destructively interfere with and/or negate vibrations arising from the movement of some or all of the set-up link 126. In some embodiment, the variable damping unit can be used in an active damper and/or in a semi-active damper. In one exemplary embodiment, one or several variable damping units having an adjustable damping coefficient can be used to create a semi-active damper, and in one exemplary embodiment, one or several variable damping units comprising one or several actuators that can be used to move all or portions of the damper, or to generate one or several forces or accelerations in all or portions of MIRS 10, can be used to create an active damper and/or to actively damp MIRS 10.

The damping units 1420 can comprise a variety of types, shapes, and sizes. In some embodiments, the damping units 1420 can be configured to damp movements of the top plate 1402 relative to the bottom plate 1406. In one embodiment, these movements can include one or several motions of the top plate 1402 and bottom plate 1406 with respect to each other in one or several of the six Cartesian degrees of freedom. In some embodiments, the degrees of freedom in which movements can occur, and therefore in which movements can be damped can depend on the design of the specific damper. In one embodiment of the damper 1400 depicted in FIG. 14, the damper 1400 can be constrained in each of the three linear degrees of freedom and can deflect in any of the three orthogonal rotary degrees of freedom as indicated by pitch, roll, and yaw in that figure, and in another embodiment of the damper 1400 depicted in FIG. 14, the damper 1400 can deflect in any of the three orthogonal rotary degrees of freedom and in any of the three linear degrees of freedom. In some embodiments, embodiments, roll indicated in FIG. 14 can correspond to torsion, and pitch and/or yaw indicated in FIG. 14 can correspond to bending.

Figure 15:
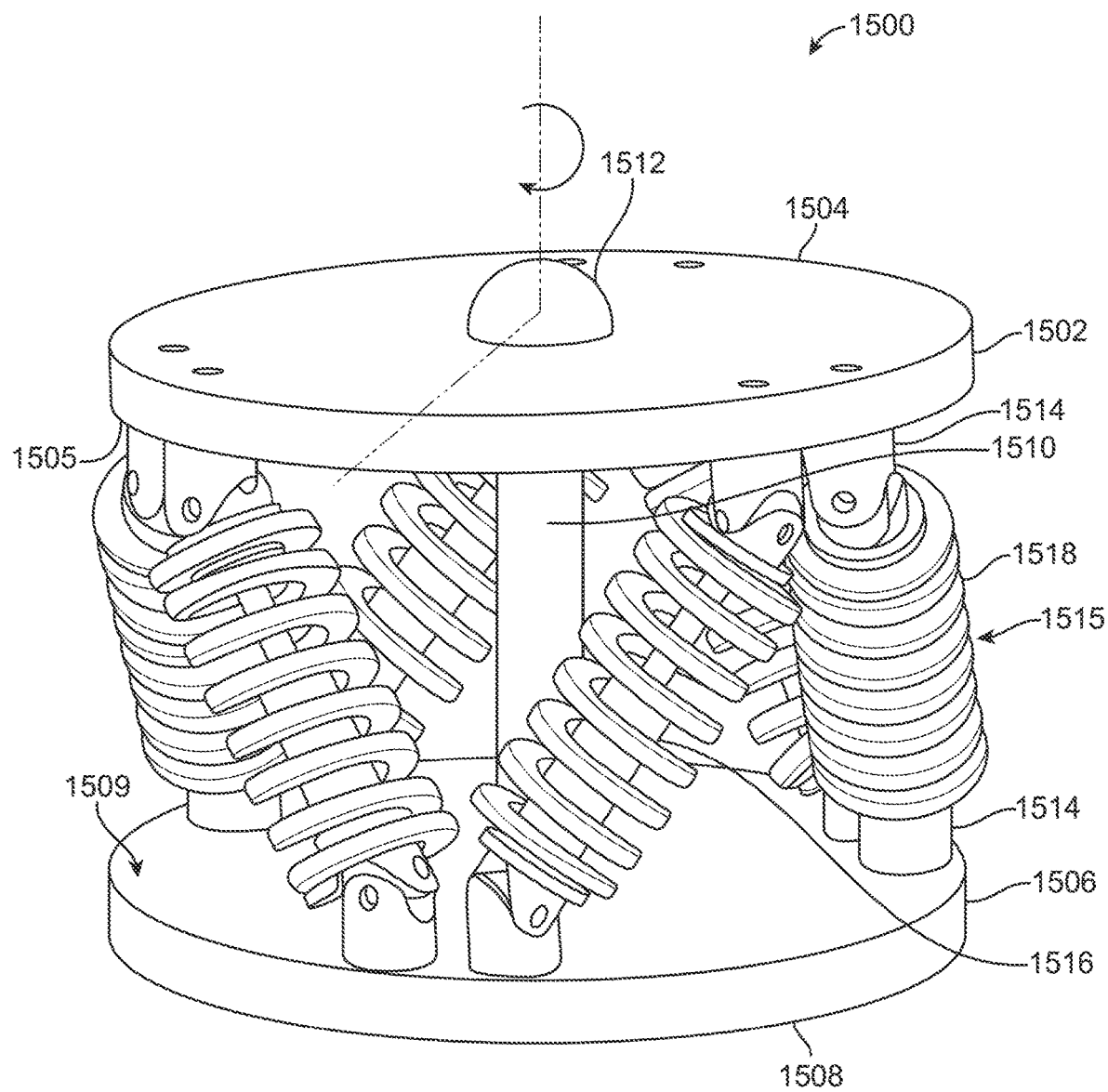
FIG. 15 is a perspective view of an alternative embodiment of a damper for use with the robotic surgery system.

FIG. 15 is a perspective view of one example embodiment of a damper 1500, which damper 1500 can be a damping platform such as 3 DOF damping platform, and specifically can be a hexapod. The damper 1500 of FIG. 15 includes a top plate 1502 having a top surface 1504 and a reverse bottom surface 1505, and a bottom plate 1506 having a bottom surface 1508 and a reverse top surface 1509. The plates 1502, 1506 can be the same or different than the plates 1402, 1406 disclosed above. In some embodiments, damper 1500 can be constrained in each of the three linear degrees of freedom and can deflect in any of the three orthogonal rotary degrees of freedom.

The top plate 1502 and the bottom plate 1510 can be connected by a shaft, and specifically by axial shaft 1510. As seen in FIG. 15, the axial shaft 1510 can connect to the top plate 1502 via a ball joint 1512 that can allow angular and rotational movement of the top plate 1502 with respect to the bottom plate 1506. In some embodiments, the axial shaft 1510 can connect to the bottom plate via a ball joint similar to ball joint 1512, and in some embodiments, the axial shaft 1510 can rigidly connect to the bottom plate 1506, and in one embodiment, can be cantilevered from the bottom plate 1506.

The shaft 1510 can comprise a variety of shapes and sizes and can be made from a variety of materials. In some embodiments, the axial shaft 1510 can be sized and shaped, and made from a material to withstand the forces applied to it during the damping of vibrations arising from the movement of portions of the robotic surgery system 140. In some embodiments, the axial shaft 1510, and particularly in the embodiment of FIG. 15, the axial shaft can comprise a rigid member.

In some embodiments, the top and bottom plates 1502, 1506 can include a plurality of mounts 1514 that can connect one or several damping systems 1515, that can be either passive or variable, to the top and bottom plates 1502, 1506. In some embodiments, these mount 1514 can comprise 3-DOF mounts similar to those disclosed with respect to FIG. 14. In some embodiments, the damping system 1515 can be configured to damp motion as well as provide a restorative force in response to a motion damped by the damping system 1515. In the embodiment of FIG. 15, the damping system 1515 comprises a damping unit 1516 and one or several springs 1518, also referred to herein as spring elements, associated with one or several damping units 1516. In some embodiments, the damping unit 1516 can be either passive or variable, and can have the same or different properties and attributes as the damping unit 1420 of FIG. 14, In one embodiment, a spring 1518 can be uniquely associated with each damping unit 1516 of the damping system 1515. In some embodiments, the spring 1518 associated with the damping unit 1516 can be positioned proximate to the damping unit 1516, and in some embodiments, the spring 1518 and the damping unit 1516 can be integrated into a combined damping system 1515, such as, for example, the coil-over springs shown in FIG. 15.

The damper 1500 can comprise any desired number of damping systems 1515. In some embodiments, the damper 1500 can comprise 1, 2, 3, 4, 5, 6, 7, 8, 9, 10, 15, 20, 30, 50, 100, and/or any other or intermediate number of damping systems 1515, damping units 1516, and/or springs 1518.

Figure 16:
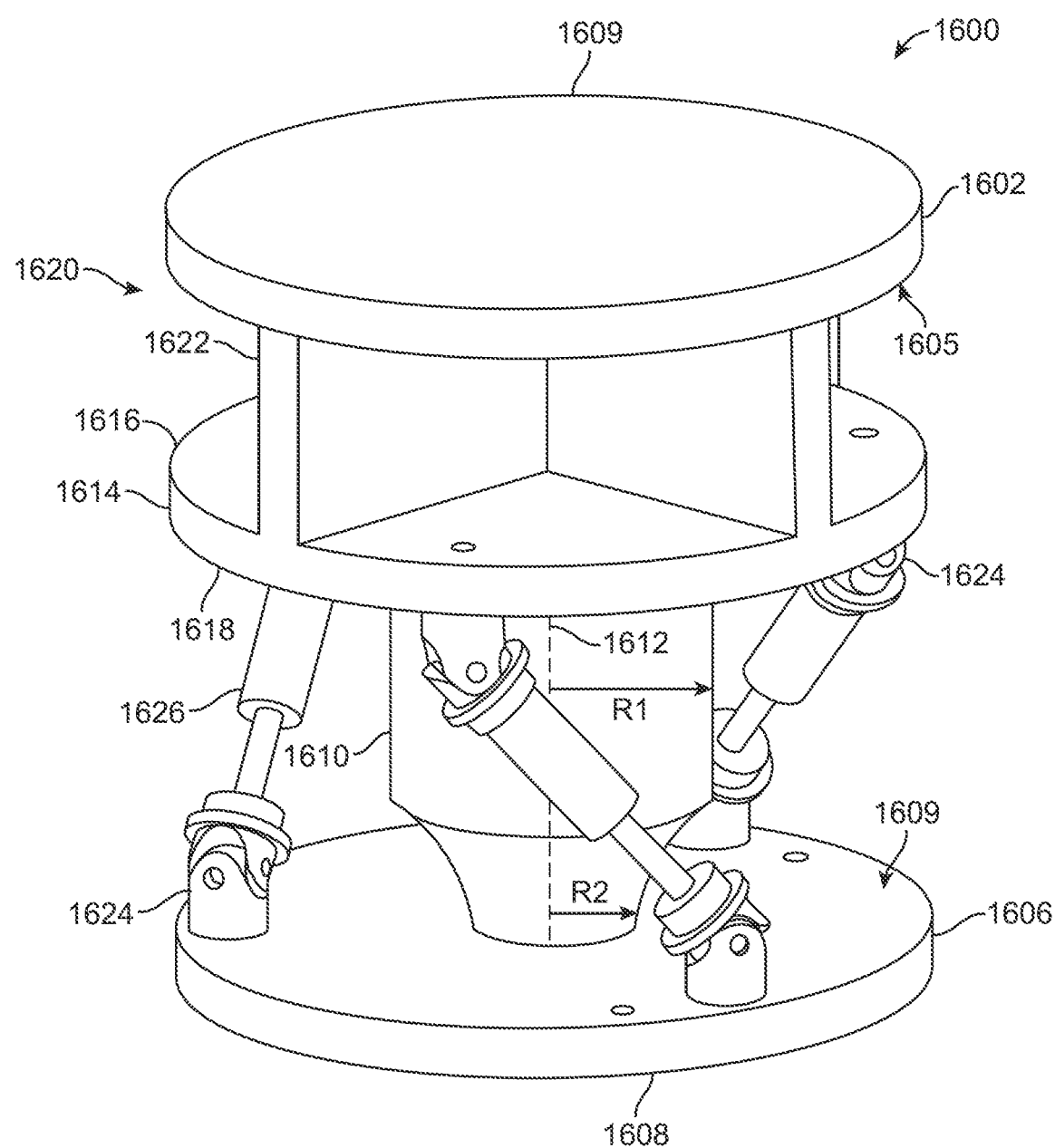
FIG. 16 is a perspective view of another alternative embodiment of a damper for use with the robotic surgery system.

FIG. 16 is a perspective view of one example embodiment of a damper 1600. Similar to damper 1400, damper 1600 includes a top plate 1602 having a top surface 1604 and a reverse bottom surface 1605, and a bottom plate 1606 having a bottom surface 1608 and a reverse top surface 1609. The top and bottom plates 1602. 1606 can be connected, at least in part, by an torsional/bending flexure 1610 that can extend along axis 1612.

In the embodiment depicted in FIG. 16, the top plate 1602 and the bottom plate 1606 can be separated by a middle plate 1614 that can have a top surface 1616 and a bottom surface 1618. The middle plate 1614 can be made of the same or different materials than one or both of the top and bottom plates 1602, 1606. In the embodiment of FIG. 16, the flexure 1610 can extend from the top surface 1609 of the bottom plate 1606 to the bottom surface 1618 of the middle plate 1614, which middle plate 1614 can be connected to the top plate 1602 via radial structure 1620, also referred to herein as a radial flexure. In some embodiments, the radial structure 1620 can be made of one or more vertical walls 1622 or other structure that extend outward from a center location. In some embodiments, the radial structure 1620 can be configured to deflect in response to a torsional force around the damper's longitudinal axis (axial torsion) applied to one or both of the top plate 1602 and the bottom plate 1606. In some embodiments, the vertical walls 1622 of the radial structure 1620 can be made of an elastically deformable material to allow the deformation of the radial structure 1620 in response to these applied forces, and in some embodiments, the vertical walls 1622 can be arranged to create one or several shapes such as, for example, a cross/cruciform, an x-shape, a y-shape, a five-spoke shape, and the like, as seen in plane extending through the radial structure 1620 between the top plate 1602 and the middle plate 1614.

The damper 1600 can include a plurality of mounts 1624 that can located on and/or attached to one or both of the bottom plate 1606 and the middle plate 1614. In some embodiments, these mounts 1624 can be used to connect one or several damping units 1626, which damping units 1626 can be variable or passive, to one or both of the bottom plate 1606 and the middle plate 1614. These mounts 1624 can comprise 3-DOF mounts similar to those disclosed above with respect to FIG. 14. Thus, as shown in FIG. 16 the bottom portion of damper 1600 may be optionally configured as generally described above for damper 1400 (FIG. 14), or it may be optionally configured as shown for other dampers such as damper 1500 (FIG. 15).

Figure 17:
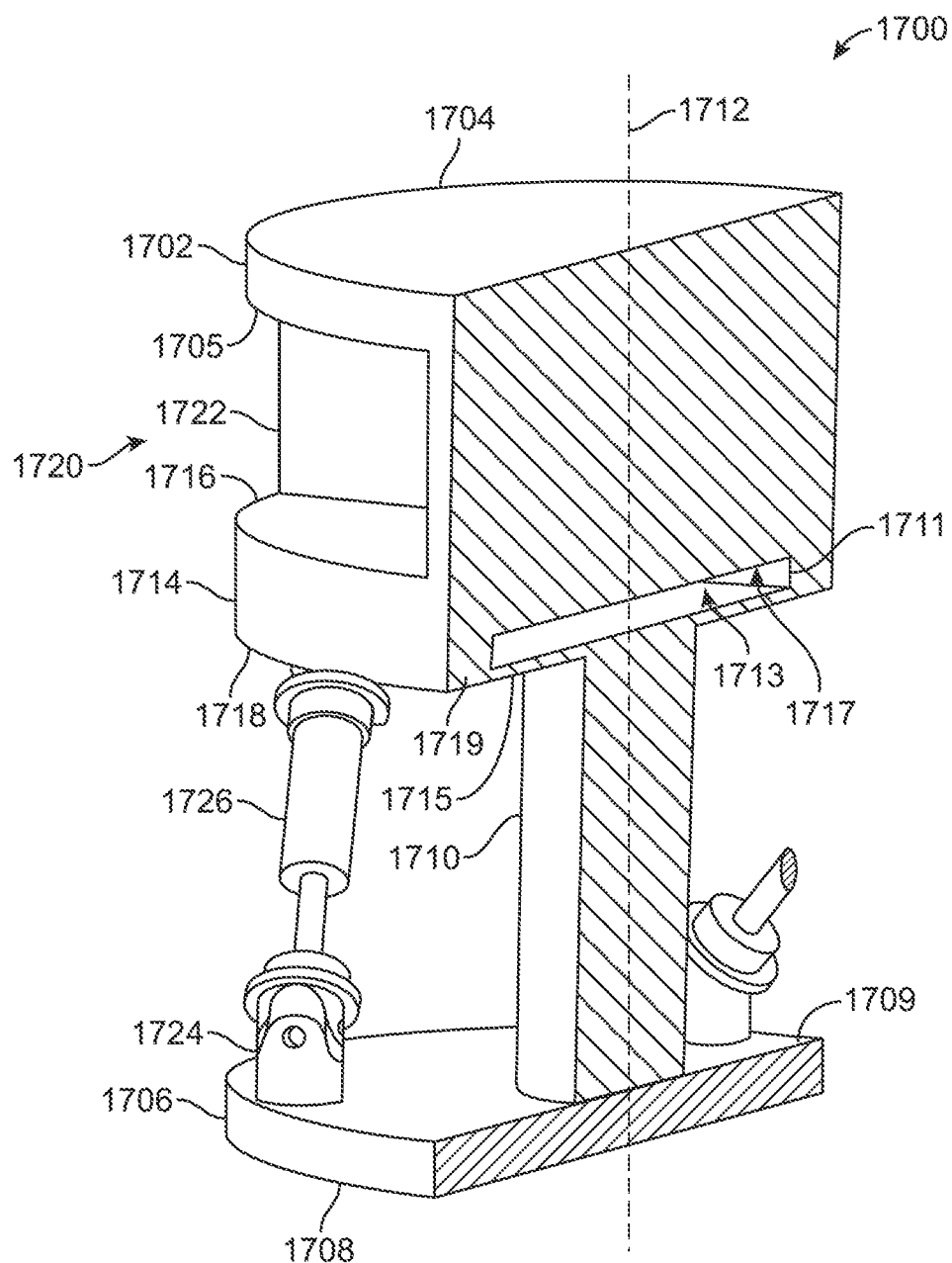
FIG. 17 is a perspective view of another alternative embodiment of a damper for use with the robotic surgery system.

FIG. 17 is a perspective view of one example embodiment of a damper 1700. Similar to damper 1600, damper 1700 includes a top plate 1702 having a top surface 1704 a reverse bottom surface 1705, and a bottom plate 1706 having a bottom surface 1708 and a reverse top surface 1709. The top and bottom plates 1702. 1706 can be connected, at least in part, by an torsional/bending flexure 1710 that can extend along axis 1712.

In the embodiment depicted in FIG. 17, the top plate 1702 and the bottom plate 1706 can be separated by a middle plate 1714 that can have a top surface 1716 and a bottom surface 1718. The middle plate 1714 can be made of the same or different materials than one or both of the top and bottom plates 1702, 1706. In the embodiment of FIG. 17, the flexure 1710 can extend from the top surface 1709 of the bottom plate 1706 to the bottom surface 1718 of the middle plate 1714. In some embodiments, the bendability and elasticity of the torsional/bending flexure 1710 can be improved by the inclusion of a decoupling flexure 1711 positioned between the torsional/bending flexure 1710 and the middle plate 1714. In the embodiment depicted in FIG. 17, the decoupling flexure 1711 comprises a void 1713 within the middle plate 1714. The void 1713 is defined by a thin plate 1715 located proximate to the bottom surface 1718 of the middle plate 1714, a void top surface 1717 positioned opposite the thin plate 1715, and a perimeter side wall 1719 that extends around all or a portion of the perimeter of the void 1711 and connects the thin plate 1715 to the void top surface 1717. As seen in FIG. 17, the torsional/bending flexure 1710 connects with the middle plate 1714 via the thin plate 1715. In some embodiments, the void 1713 can increase the ability of the damper 1700 to damp vibrations/movements along one or several Cartesian degrees of freedom. In the embodiment depicted in FIG. 17, for example, the void 1713 may allow a linear displacement of the middle plate 1714 with respect to the bottom plate 1706 along longitudinal axis 1712. Further, the void 1713 may allow rotations of the middle plate 1714 with respect to the bottom plate 1706 about axes perpendicular to the longitudinal axis 1712.

In some embodiments, the middle plate 1714 can be connected to the top plate 1702 via radial structure 1720 made of one or more vertical walls 1722 or other structure that extend outward from a center location. In some embodiments, the radial structure 1720 can be configured to deflect in response to a torsional force around the damper's longitudinal axis (axial torsion) applied to one or both of the top plate 1702 and the bottom plate 1706. In some embodiments, the vertical walls 1722 of the radial structure 1720 can be made of an elastically deformable material to allow the deformation of the radial structure 1720 in response to these applied forces, and in some embodiments, the vertical walls 1722 can be arranged to create one or several shapes such as, for example, a cross/cruciform, an x-shape, a y-shape, a five-spoke shape, and the like.

The damper 1700 can include a plurality of mounts 1724 that can located on and/or attached to one or both of the bottom plate 1706 and the middle plate 1714. These mounts 1724 can comprise 3-DOF mounts similar to those disclosed above with respect to FIG. 14. In some embodiments, these mounts 1724 can be used to connect one or several damping units 1726 to one or both of the bottom plate 1706 and the middle plate 1714. The one or several damping units 1726 can be passive or variable damping units.

Figure 18:
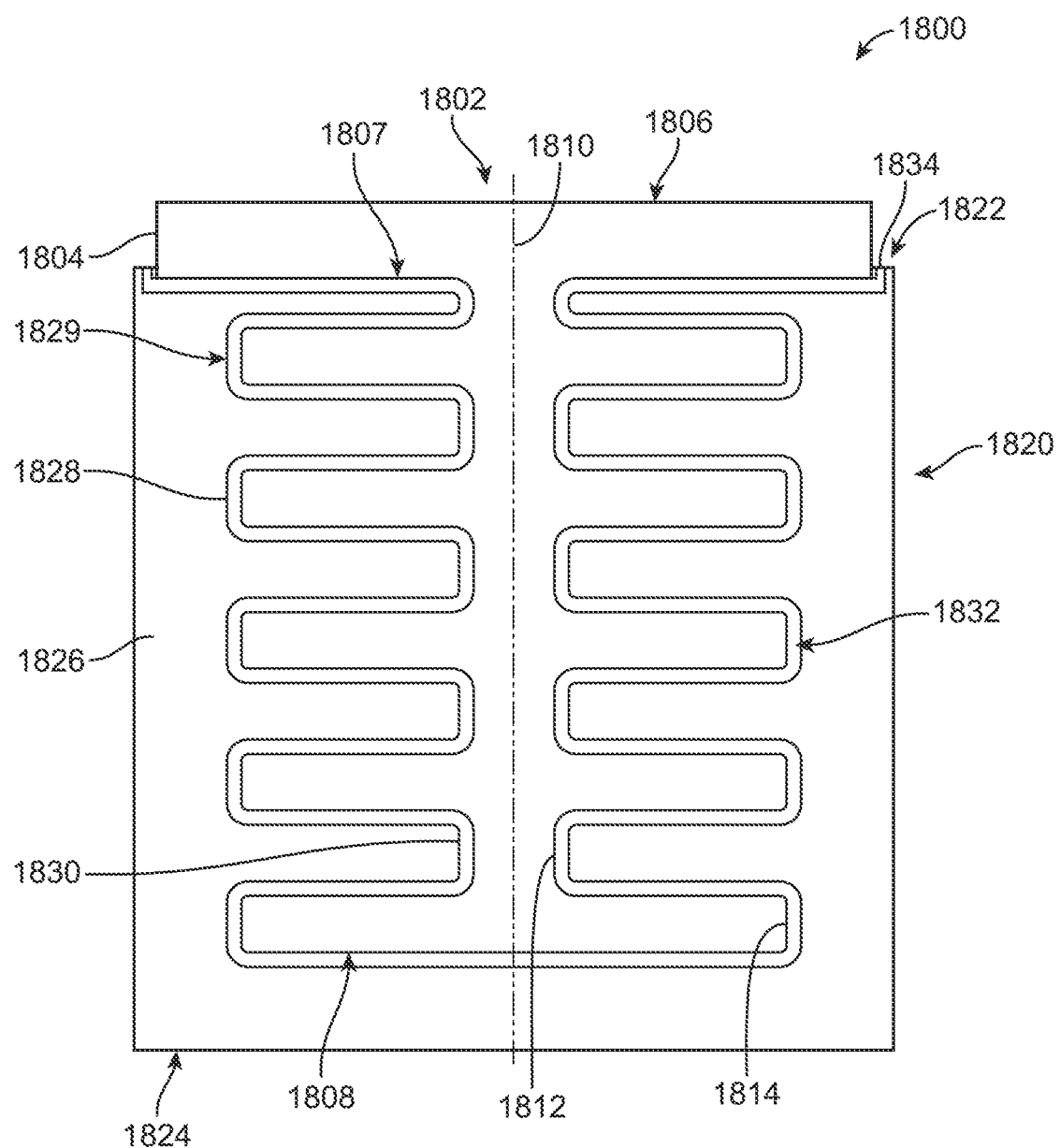
FIG. 18 is a section view of one embodiment of a squeeze film damper for use with the robotic surgery system.

FIG. 18 is a section view of one example embodiment of a damper 1800, and specifically of an interdigitated damper. In some embodiments, the damper 1800 can comprise a squeeze film damper. The damper 1800 includes a first piece 1802. The first piece 1802 can comprise a variety of shapes and sizes, and can be made from a variety of materials. In some embodiments, the first piece 1802 can be made of a material, and sized and shaped so as to be rigid for the loads applied to the damper 1800.

The first piece 1800 can include a top plate 1804 having a top surface 1806 and a reverse bottom surface 1807. The first piece 1802 can further include a bottom surface 1808 located at the opposite end of the first piece 1802 as compared to the top surface 1806 of the top plate 1804.

As seen in FIG. 18, a longitudinal axis 1810 can extend through the center of the first piece 1802 between the top surface 1806 of the top plate 1804 and the bottom surface 1808 of the first piece 1802. The first piece can include a shaft 1812 that extends along the longitudinal axis 1810 and from the bottom surface 1807 of the top plate 1804 to the bottom surface 1808 of the first piece 1802. This shaft 1812 can comprise an elongate member that can be the same, or different material than the other portions of the first piece 1802.

In some embodiments, one or several protrusions 1814 can extend away from the shaft 1812. In some embodiments, these protrusions 1814 can be regularly or irregularly spaced along the length of the shaft 1812, as well as regularly or irregularly spaced around the perimeter of the shaft 1812. The protrusions 1814 can comprise a variety of shapes and sizes. In one embodiment, the protrusions 1814 can each comprise a disk-shaped member radially extending from either some or all of the perimeter of the shaft 1812. In some embodiments, the first piece 1802 can include 1, 2, 3, 4, 5, 6, 7, 8, 9, 10, 15, 20, and/or any other or intermediate number of protrusions 1814.

The damper 1800 can include a second piece 1820 that can be sized and shaped to receive some or all of the first piece 1802. The second piece 1820 can comprise a variety of shapes and sizes, and can be made from a variety of materials. In some embodiments, the second piece 1820 can be made of a material, and sized and shaped so as to be rigid for the loads applied to the damper 1800.

The second piece 1820 can include a top surface 1822, a reverse bottom surface 1824, and a side wall 1826 extending from the top surface 1822 to the bottom surface 1824 of the second piece 1820. In some embodiments, the side wall 1826 can include an interior wall 1828. In the embodiment depicted in FIG. 18, the combination of the top and bottom surfaces 1822, 1824 and the interior wall 1828 can bound and/or partially bound an internal volume 1829 of the second piece 1820. In some embodiments, the internal volume 1829 of the second piece 1820 can receive some or all of the first piece 1802, and as depicted in FIG. 18, the internal volume 1829 can receive the shaft 1812 and the protrusions 1814 of the first piece 1802.

As seen in FIG. 18, in some embodiments, one or several mating protrusions 1830 can extend from the interior wall 1828 of the second piece 1820 towards the longitudinal axis 1810. In some embodiments, these mating protrusions 1830 can be regularly or irregularly spaced along the length of the interior wall 1828, as well as regularly or irregularly spaced around the perimeter of the interior wall. The mating protrusions 1830 can comprise a variety of shapes and sizes. In one embodiment, the mating protrusions 1830 can each comprise an annular-shaped member extending radially inward from either some or all of the perimeter of the interior wall 1828. In some embodiments, the second piece 1820 can include 1, 2, 3, 4, 5, 6, 7, 8, 9, 10, 15, 20, and/or any other or intermediate number of mating protrusions 1830.

In some embodiments, and as depicted in FIG. 18, the protrusions 1814 and the mating protrusions 1830 can be positioned such that some or all of the mating protrusions 1830 extend between pairs of protrusions 1814. Similarly, in some embodiments, the protrusions 1814 and the mating protrusions 1830 can be sized and shaped such that when the first piece 1802 is received within the internal volume 1829 of the second piece 1820, the protrusions 1814 and the mating protrusions 1830 are interdigitated that such that a film space 1832 exists between the protrusions and the mating protrusions 1830. In some embodiments, the film space 1832 can be filled with a material that can be a fluid of a fluid like substance, such as powder. In some embodiments, the fluid can comprise a viscous fluid and/or a highly viscous fluid. In some embodiments, the fluid can have a viscosity of at least 20 centipoise, 50 centipoise, 100 centipoise, 200 centipoise, 500 centipoise, 1000 centipoise, 1500 centipoise, 2000 centipoise, and/or of any other or intermediate value. In some embodiments, a fluid is a highly viscous fluid when it has a viscosity of at least 200 centipoise. In some embodiments, the material in the film space can be selected to provide the desired damping level in the damper 1800. In some embodiments, and as seen in FIG. 18, the film space 1832 can be sealed by, for example, seal 1834. The seal 1834 can be any type of seal including, for example, a gasket, an O-ring, or the like.

In some embodiments, a spring can extend from the first piece 1802 to the second piece 1820. In some embodiments, the spring can be configured to apply a restorative force to the first and second pieces 1802, 1820 after they have been moved relative to each other. In some embodiments, the spring can be a 1 DOF spring, a 2 DOF spring, a 3 DOF spring, a 4 DOF spring, a 5 DOF spring, a 6 DOF spring, or a spring active along any other number or combination of DOFs. In one embodiment, the spring can be a torsion spring, a compression spring, a tension spring, or any other kind of spring. The spring can comprise any desired shape and size, and can be made from any desired material. In some embodiments, the spring can be designed so as to provide a desire strength of restorative force to the first and second pieces 1802, 1820.

Figure 19:
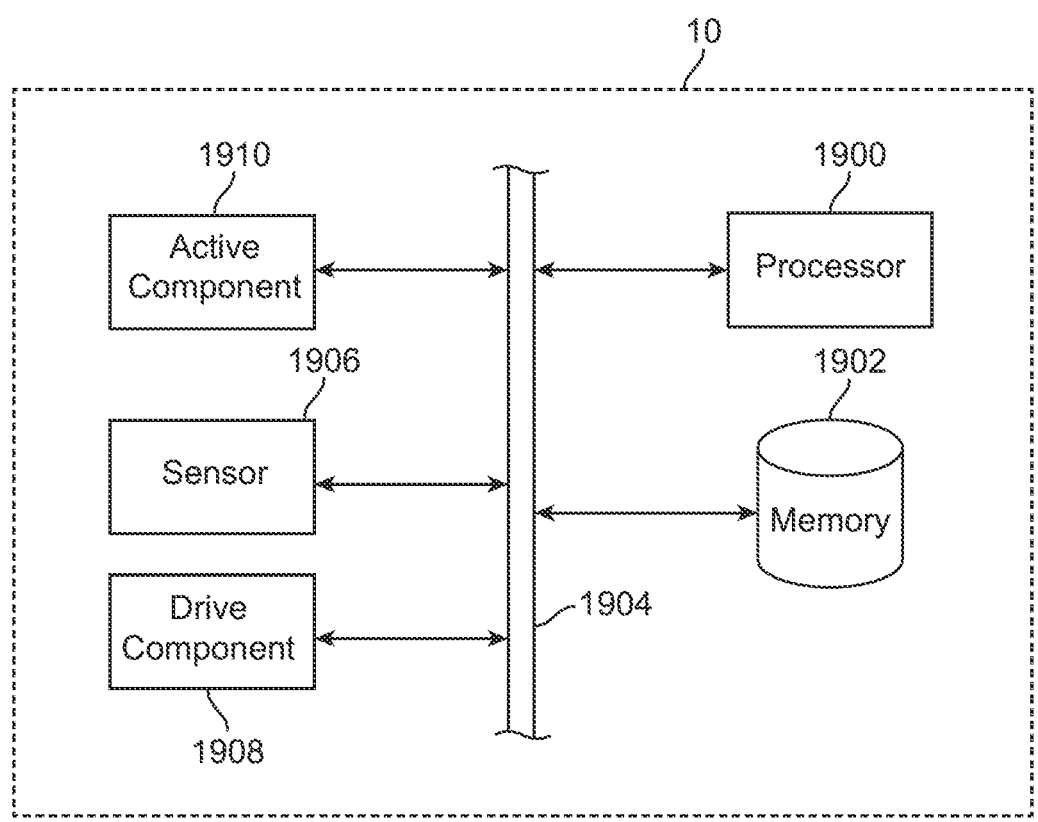
FIG. 19 is a functional illustration of one embodiment of a surgical system.

FIG. 19 is a schematic illustration of one embodiment of the MIRS 10, and specifically, one embodiment of functional components of the MIRS 10 that can be used in actively or semi-actively damping vibrations arising within portions of the MIRS 10. As seen in FIG. 19, MIRS 10 includes processor 1900, which includes a memory and an arithmetic or logic unit. The processor 1900 can be processor 58, which can be located in any component of MIRS 10 or distributed among two or more system components, and in one embodiment, the processor 1900 can be located in the equipment cart 24. In some embodiments, the processor 1900 can provide instructions to and receive information from the other components of MIRS 10, and specifically provide instructions to and receive information from the other components of MIRS 10 for damping of vibrations. The processor 1900 can act according to stored instructions, which stored instructions can be located in memory, associated with the processor 1900, and/or in other components of MIRS 10. The processor 1900 can, in accordance with stored instructions, make decisions. The processor can comprise a microprocessor, such as a microprocessor from Intel® or Advanced Micro Devices, Inc.®, or the like.

In some embodiments, the stored instructions directing the operation of the processor may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as memory 1902.

In some embodiments, the memory 1902 may represent one or more memories for storing data, including read only memory (ROM), random access memory (RAM), magnetic RAM, core memory, magnetic disk storage mediums, optical storage mediums, flash memory devices and/or other machine readable mediums for storing information. In some embodiments, the memory 1902 may be implemented within the processor or external to the processor. In some embodiments, the memory 1902 can be any type of long term, short term, volatile, nonvolatile, or other storage medium and is not to be limited to any particular type of memory or number of memories, or type of media upon which memory is stored. In some embodiments, the memory 1902 can include, for example, one or both of volatile and nonvolatile memory. In one specific embodiment, the memory 1902 can include a volatile portion such as RANI memory, and a nonvolatile portion such as flash memory.

The processor 1900 can be communicatingly connected with the memory 1902 by connection network 1904. In some embodiments, the connection network 1904 can be wired connection network 1904 and/or a wireless connection network 104. In one embodiment in which the connection network 1904 comprises a wired connection, the connection network 1904 can be one or several buses.

The processor 1900 can receive information from a sensor 1906 and/or a drive component 1908. In some embodiments, the sensor 1906 can be the one or several sensors 1200 that can detect a property of the movement of, for example, the set-up linkage 126 and/or a position of the set-up linkage 126. In one embodiment, the sensor 1906 can include an acceleration sensor such as an accelerometer configured to sense an acceleration of all or portions of the set-up linkage 126, and in some embodiments, the sensor 1906 can include a position sensor configured to sense a position of all or portions of the set-up linkage. In some embodiments, the property of movement of the set-up linkage 126 can be, for example, the detection of a vibration, the detection of an acceleration, the detection of a jerk, or the like. In some embodiments, the drive component 1908 can comprise the one or several components or features that can be controlled to cause the movement of parts of the robotic surgical system 140 including, for example, some or all of the set-up linkage 126. In some embodiments, the drive component 1908 can comprise one or several motors, actuators, or the like.

The processor 1900 can be configured to, with the information received form the sensor 1906 and/or drive component 1908, determine an acceleration and/or vibration occurring in part of MIRS 10, including in all or a portion of the set-up linkage 126, estimate and/or determine an acceleration and/or vibration that will occur in part of MIRS 10, including in all or a portion of the set-up linkage 126, calculate one or several damping solutions to mitigate any present or estimated vibrations, and control components of the MIRS 10 according to the one or several damping solutions.

In one embodiment, the processor 1900 can be configured to estimate and/or determine an acceleration and/or vibration occurring in one or several set-up linkages 126 and to generate one or several damping solutions to mitigate that vibration in those one or several set-up linkages 126. This can include, for example, identifying that the vibration is arising in the one or several set-up linkages 126 and damping the one or several set-up linkages 126. In some embodiments, this can include, for example, identifying that the source of the vibration is a different set-up linkage 126 than the set-up linkage 126 where the vibration is being experienced and/or determined. In some such embodiments, the vibration at the set-up linkage 126 where the vibration is being experienced and/or determined can be mitigated by damping the set-up linkage 126 where the vibration is being experienced and/or determined, and in some such embodiments, the vibration at the set-up linkage 126 where the vibration is being experienced and/or determined can be mitigated by damping the set-up linkage 126 that is the source of the vibration.

In some embodiments, the processor 1900 can be configured to estimate and/or determine an acceleration and/or vibration occurring in one or several set-up linkages 126 and to generate one or several damping solutions to mitigate that vibration in one or several other set-up linkages 126. Thus, in one embodiment, the processor 1900 can be configured to mitigate a vibration within one or several of the set-up linkages 126 via the damping solution, and in one embodiment, the processor 1900 can be configured to mitigate the effects of a vibration arising in one or several of the set-up linkages 126 on one or several other set-up linkages 126.

As the inertial properties of the set-up linkage 126 can change based on the position of the set-up linkage 126, in some embodiments, the processor 1900 can be configured to receive information indicating the position of the set-up linkage 126, or components thereof, and use that position information to determine one or several inertial/dynamic properties of the current position/configuration of the set-up linkage 126. In some embodiments, the determined one or several inertial/dynamic properties of the current position/configuration of the set-up linkage 126 can be used in the generation of the damping solution.

In some embodiments, the processor can generate one or several control signals to control the operation of drive component 1908 and/or variable component 1910. In some embodiments, these control signals can include, for example, controls signals to direct the movement of some or all of MIRS 10 including, for example, some or all of set-up linkage 126. Such control signals can be provided to the drive component 1908 to control the movement of all or portions of MIRS 10, including in all or a portion of the set-up linkage 126. In one embodiment, for example, the processor 1900 can receive a command to move a portion of MIRS 10 and, based on the command, generate control signals for the drive component 1908. In some such embodiments, the processor 1900 can also estimate a vibration arising from such a movement and generate a damping solution based on this estimated vibration. In some embodiments, the processor 1900 can command the drive component 1908 to move the portion of MIRS 10 and can receive information from the sensor 1906 regarding accelerations and/or vibrations caused by the movement of the portion of MIRS 10. The processor 1900 can use this information to calculate a damping solution.

In some embodiments, the control signals can be generated to control the damping of MIRS 10 via the control of variable component 1910. In some embodiments, the variable component 1910 can be a voice coil and/or a variable component of one of the damping units discussed above such as, for example, an actuator. In some embodiments, the control signal that controls the damping of MIRS 10 can embody the damping solution and can direct the variable component 1910 to affect its damping, which can include affecting its damping coefficient, or in other words, the damping coefficient of the therewith associated damping unit. The interaction of these modules will be discussed at greater length below with respect to the following flowcharts and processes for controlling MIRS 10.

Figure 20:
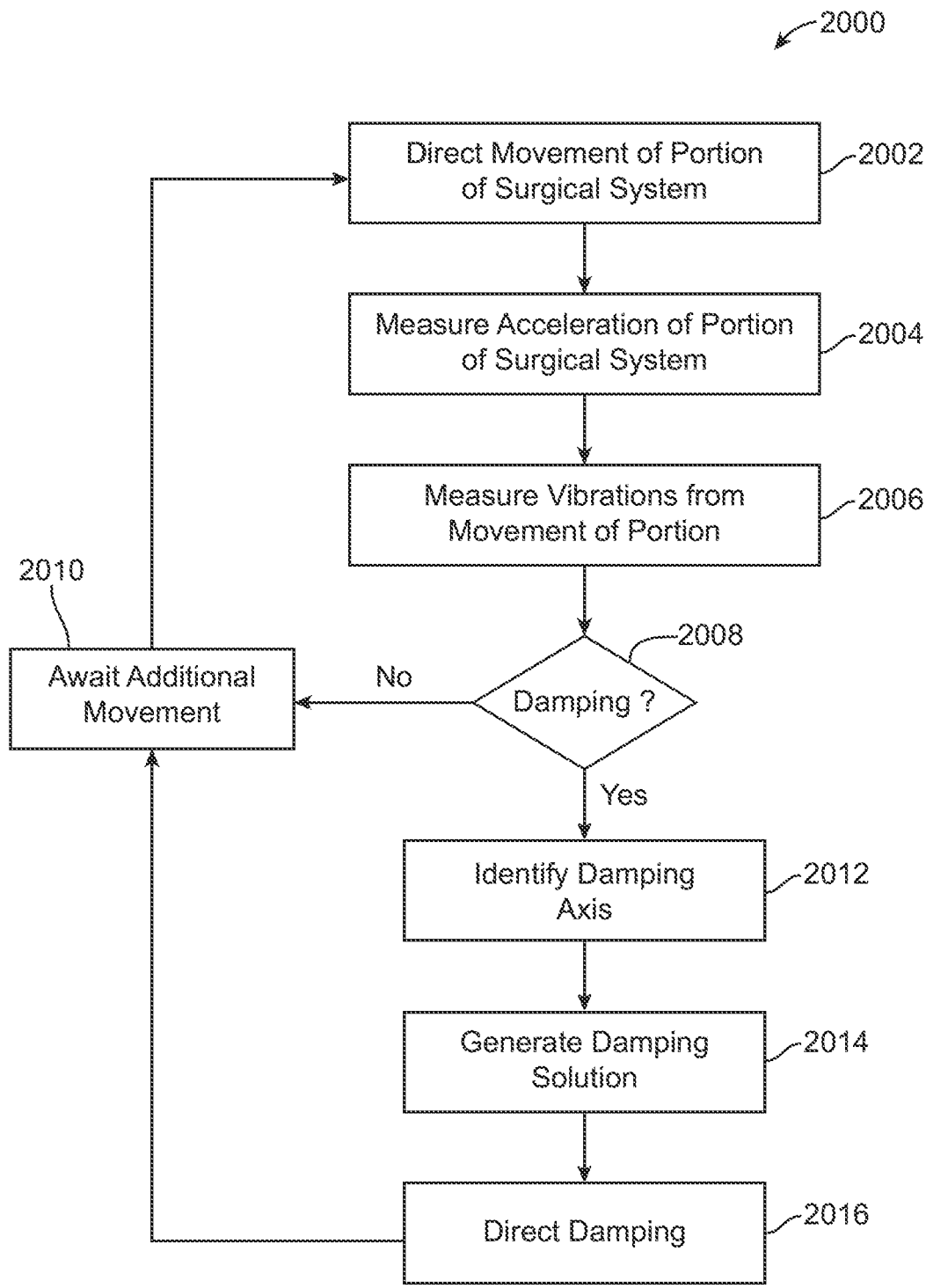
FIG. 20 is a flowchart illustrating one embodiment of a process for feedback based variable damping.

FIG. 20 is a flowchart illustrating one embodiment of a process 2000 for mitigating vibration in MIRS 10. The process 2000 comprises one embodiment of feedback based damping that can be applied to MIRS 10, and specifically to one or several set-up linkages 126 of MIRS 10. The process 2000 can be performed using the functional components depicted in FIG. 19.

The process begins at block 2002 wherein the processor 1900 directs the movement of a portion of the MIRS 10, and specifically of the robotic surgical system 140. In some embodiments, this can include the control of one or several of the set-up linkages 126 by the processor 1900. In some embodiments, this step can include receiving a command from the surgeon's console 16, generating the command signal to control the drive component 1908, and controlling the drive component 1908 according to the generated command signal.

After the movement of the portion of the MIRS 10 has been directed, process 2000 proceeds to block 2004, wherein an acceleration parameter, or other motion related parameter, of a portion of the MIRS 10 is measured. In some embodiments, this portion of the MIRS 10 for which the acceleration parameter is received can be the portion that is being moved according to the command signal generated in block 2002, and in some embodiments, this portion of the MIRS 10 for which the acceleration parameter is received can be a portion other than the portion that is being moved according to the command signal generated in block 2002.

In one embodiment, the acceleration parameter can be a value identifying the acceleration of all or portions of MIRS 10. Similarly, in one embodiment, the motion related parameter can identify, for example, a position, velocity, a jerk, or the like of all or portions of MIRS 10. In some embodiments, this acceleration parameter can be measured by the sensor 1906, and the acceleration parameter can be a value identifying an acceleration of a portion of the MIRS 10 such as, for example, the portion of the MIRS 10 moved in block 2002.

In one embodiment, the acceleration parameter can be used to determine and/or identify one or several vibrations occurring within the set-up linkage 126. In one embodiment, for example, an acceleration sensed by sensor 1906 can be compared with a value identifying a predicted and/or expected acceleration of the portion of the set-up linkage 126 containing the sensor 1906. In one embodiment, this value identifying the predicted and/or expected acceleration can be calculated based on the move command received from the surgeon's console 16, the position of the set-up linkage 126, and/or on one or several dynamic/inertial properties of the set-up linkage. In such an embodiment, the difference between the measured acceleration and the value identifying the predicted and/or expected acceleration can characterize the acceleration of a vibration occurring at the sensor 1906.

In some embodiments, and as a part of block 2004, a position sensor can sense the position of the set-up linkage 126. This position can include the position of one or several joints and/or components of the set-up linkage 126. As mentioned above, this information can be used to determine one or several inertial/dynamic properties of the set-up linkage 126.

After the acceleration parameter has been measured, the process 2000 proceeds to block 2006, wherein a vibration parameter of a portion of the MIRS 10 is measured. In some embodiments, this vibration parameter can be measured by the sensor 1906, and the vibration parameter can be a value identifying a vibration of a portion of the MIRS 10 such as, for example, the portion of the MIRS 10 moved in block 2002. The vibration parameter can be any parameter that characterizes a vibration such as, for example, the frequency, wavelength, amplitude, decay rate, or the like.

After the vibration parameter has been measured, process 2000 proceeds to decision state 2008, wherein it is determined whether to damp the MIRS 10. In some embodiments, this determination can include a comparison of the measured parameters including, for example, the measured acceleration parameter and the vibration parameter to a threshold value. If one or neither of the parameters exceeds the threshold value, then a vibration can be identified as unsuitable for damping, and process 2000 can proceed to block 2010 and wait for a next, or additional movement. In such an embodiment, after the next or additional movement has been received, process 2000 proceeds to block 2002 and continues as outlined above. Thus, in some embodiments, a vibration is identified by comparing a sensed acceleration to a first, predicted value, and it is determined whether to mitigate the identified vibration by comparing the identified vibration to a second, threshold value.

Returning again to decision state 2008, if one or both of the motion parameters exceed the threshold value, then the vibration can be identified as suitable for damping. In such an embodiment, process 2000 proceeds to block 2012, wherein the damping axes are determined. In some embodiments, the damping axes can be the axes along which the vibrations are occurring. In some embodiments, the vibration can occur along one axis, and in some embodiments, the vibration can occur along a plurality of axes. In some embodiments, determining the axes of the vibration can be performed with data received from the sensor 1906.

After the one or more damping axes have been determined, the process 2000 proceeds to block 2014, wherein a damping solution is identified. In some embodiments, the damping solution can comprise one or several actions to mitigate the measured vibration. These can include, for example, instructions to change the damping coefficient of a damper, instructions to control a voice coil, and/or instructions to control the behavior of an actuator.

After the damping solution has been generated, the process 2000 proceeds to block 2016, wherein the damping is directed. In some embodiments, this can include the generation of a control signal by the processor 1900 to control one or both of the drive component 1908 and the variable component 1910, and providing the control signal to the drive component and/or the variable component 1910.

Figure 21:
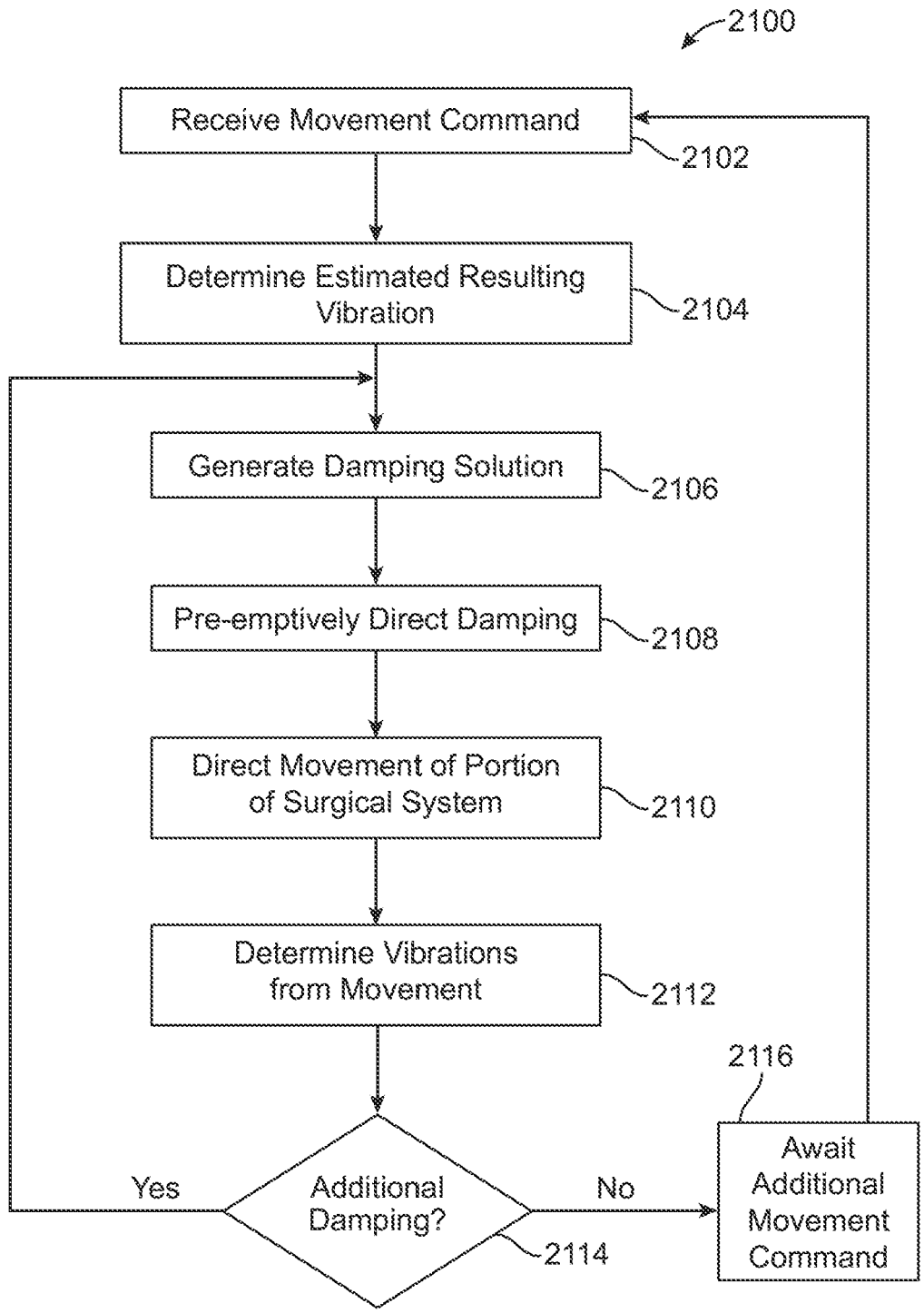
FIG. 21 is a flowchart illustrating one embodiment of a process for feed-forward based variable damping.

FIG. 21 is a flowchart illustrating one embodiment of a process 2100 for mitigating vibration in MIRS 10. The process 2100 comprises one embodiment of feed-forward based damping that can be applied to MIRS 10, and specifically to one or several set-up linkages 126 of MIRS 10. The process 2100 can be performed using the functional components depicted in FIG. 19.

The process 2100 begins at block 2102, wherein a movement command is received. In some embodiments, the motion command can be received at the processor 1900 from the surgeon's console 16. After the movement command has been received, the process 2100 proceeds to block 2104 wherein a resulting vibration is estimated. In some embodiments, this estimation can include generating the signal to control the drive component 1908 and evaluating the forces, accelerations, and/or jerks that will arise as a result of the movement command. With this information, the processor 1900 can retrieve one or several attributes of the portion of the MIRS 10 that will be moving, and more specifically of the relevant set-up linkage 126 or portions thereof. These attributes can include, for example, one or several dimensions, one or several masses, one or several rigidities and/or structural rigidities, one or several centers of mass, one or several moments of inertia, and/or the like. In some embodiments, the processor 1900 can, based on these properties and the forces, accelerations, and/or jerks that will arise as a result of the movement command, estimate resulting vibrations.

After the resulting vibrations have been estimated, the process 2100 proceeds to block 2106, wherein a damping solution is generated. In some embodiments, this step can be proceeded by a determination according to decision state 2008 of FIG. 20, wherein it is determined whether to damp the MIRS 10. In some embodiments, this determination can include a comparison of estimated resulting vibration to a threshold value. If the estimated resulting vibration does not exceed the threshold value, then a vibration can be identified as unsuitable for damping, and process 2100 can await an additional movement command, at which point process 2100 can return to block 2102.

Conversely, if the estimated resulting vibration exceeds the threshold value, then the vibration can be identified as suitable for damping. In such an embodiment, process 2100 proceeds to block 2106 wherein a damping solution is generated and/or identified. The damping solution can comprise one or several actions to mitigate the estimated vibration. These can include, for example, instructions to change the damping coefficient of a damper, instructions to control a voice coil, and/or instructions to control the behavior of an actuator. In some embodiments, this can include the identification of the damping axes of the estimated vibration.

After the damping solution has been generated, the process 2100 proceeds to block 2108, wherein the damping is pre-emptively directed. In some embodiments, the damping is pre-emptively directed in that the damping commands to one or both of the drive component 1908 and/or the variable component 1910 are sent before and/or simultaneous with the sending of the motion commands to the drive component 1908.

After the damping has been pre-emptively directed, the process 2100 proceeds to block 2110, wherein the movement of a portion of the MIRS 10, and specifically of the robotic surgical system 140 is directed. In some embodiments, this can include the sending of control signals for one or several of the set-up linkages 126. In some embodiments, this step can include generating the command signal to control the drive component 1908, and controlling the drive component 1908 according to the generated command signal.

After the movement of a portion of the MIRS 10 is directed, the process 2100 proceeds to block 2112, wherein the resulting vibrations of the movement are detected. In some embodiments, these vibrations can be vibrations that were not completely damped by the step of block 2108. In some embodiments, these vibrations can be detected by the sensor 1906. This detection can correspond to blocks 2004 and 2006 of FIG. 20.

After any resulting vibrations of the movement are detected, the process 2100 proceeds to decision state 2114, wherein it is determined if additional damping is required. In some embodiments, this determination can include a comparison of the detected vibrations to a threshold value. If detected vibrations do not exceed the threshold value, then a vibration can be identified as unsuitable for damping, and process 2100 proceeds to block 2116 and waits for a next, or additional movement. In such an embodiment, after the next or additional movement has been received, process 2100 returns to block 2102 and continues as outlined above.

Returning again to decision state 2114, if the detected vibrations exceed the threshold value, then the vibrations can be identified as suitable for damping. In such an embodiment, process 2100 returns to block 2106, and proceeds as outlined above.

Figure 22:
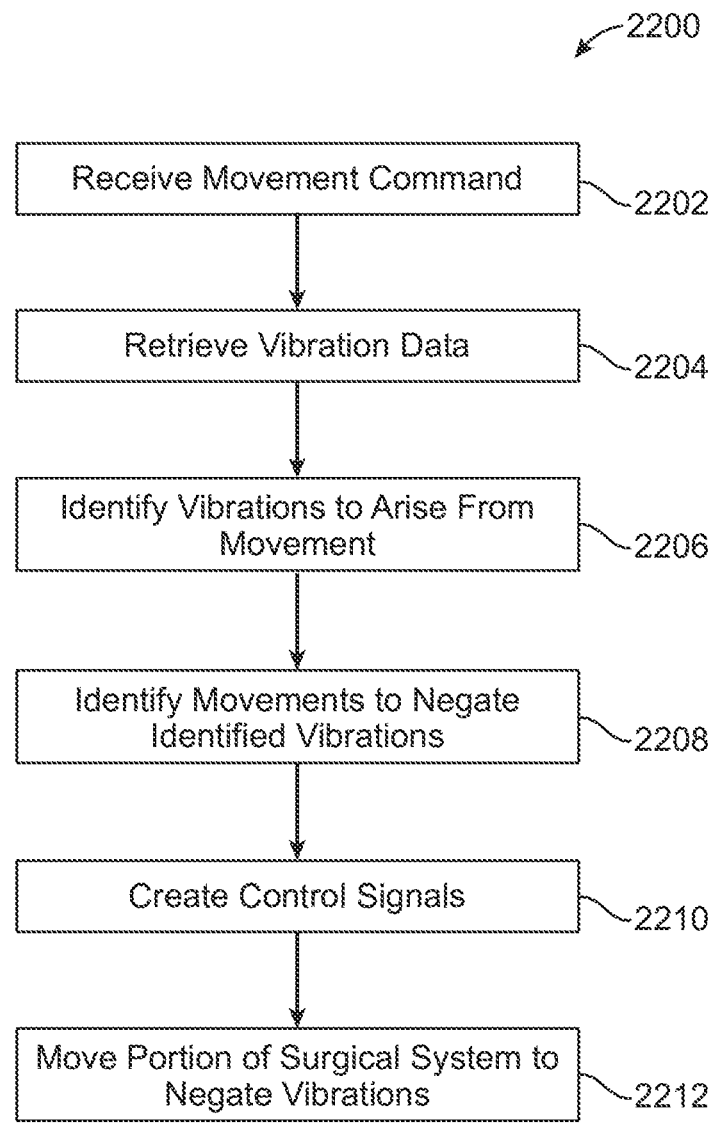
FIG. 22 is a flowchart illustrating one embodiment of a process for input shaping based variable damping.

FIG. 22 is a flowchart illustrating one embodiment of a process for input shaping to damp vibrations in MIRS 10. The process 2200 can be performed using the functional components depicted in FIG. 19.

The process 2200 begins at block 2202, wherein a movement command is received. In some embodiments, the motion command can be received at the processor 1900 from the surgeon's console 16. In some embodiments, the movement command can request the movement of one or more of the set-up linkages 126, or the surgical tools of one or more set-up linkages from a first position to a second position, and in some embodiments, the movement command can direct the velocity and/or acceleration of the one or more set-up linkages 126 for the movement from the first position to the second position. After the movement command has been received, the process 2200 proceeds to block 2204 wherein vibration data is retrieved. In some embodiments, the vibration data can comprise one or several attributes of the portion of the MIRS 10 that will be moving, such as, for example, the surgical tool and/or the set-up linkage 126, and more specifically of the relevant set-up linkage 126 or portions thereof, and in some embodiments, the vibration data can be relevant to a portion of the MIRS 10 that is not moving, but is experiencing a vibration due to the moving portion of the MIRS 10. These attributes can include, for example, one or several dimensions, one or several masses, one or several rigidities and/or structural rigidities, one or several centers of mass, one or several moments of inertia, and/or the like.

After the vibration data has been retrieved, the process 2200 proceeds to block 2206, wherein vibrations expected to arise from the commanded movement are identified. In some embodiments, this identification can include generating the signal to control the drive component 1908 and evaluating the forces, accelerations, and/or jerks that will arise as a result of the movement command. With this information, and with the retrieved vibration data, the processor 1900 can identify vibrations that are expected to arise as a result of moving the portion of MIRS 10 according to the received movement command.

After the vibrations that are expected to arise have been identified, the process 2200 proceeds to block 2208 wherein a movement profile of a portion of MIRS 10 is identified that will negate and/or minimize the expected vibrations. In some embodiments, this movement profile can be generated using the vibration data retrieved above.

After the movement profile has been identified that will negate and/or minimize the expected vibrations resulting from the received movement command, the process 2200 proceeds to block 2210, wherein one or several control signals are generated. In some embodiments, the control signals can be generated by the processor 190. After the control signals are generated, the process 2200 proceeds to block 2212, wherein the processor 1900 controls the drive component 1908 according to the control signals and the movement profile identified in block 2208. In some embodiments, this can result in moving, for example, all or a portion of the set-up linkage 126, such as the surgical tool, from a first position to a second position, and in some embodiments, can result in moving, for example, all or a portion of the set-up linkage 126, such as the surgical tool, from a first position to a second position at one or several velocities and with one or several accelerations. In some embodiments, movement according to the movement profile mitigates the expected vibrations. In some embodiments, additionally, the sensor 1906 can sense any unmitigated vibration arising due to the movement, and this vibration can be mitigated as outlined above with respect to FIGS. 20 and 21.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. Similarly, in some embodiments, one or more of the methods described herein can be, in whole or in part, combined. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system comprising:
   a linkage comprising a first link, a second link, and a damper coupling the second link to the first link;
   a processor configured to:
      receive a movement command for moving the linkage;
      determine one or more first vibrations expected to occur in the linkage as a result of performing the movement command;
      determine a movement profile for moving the linkage to reduce the one or more first vibrations; and
      drive, using a drive component, the linkage to move according to the movement profile.

2. The system of claim 1, wherein to determine the one or more first vibrations, the processor is configured to determine one or more forces, accelerations, or jerks that are expected to occur in the linkage as a result of performing the movement command.

3. The system of claim 1, wherein the one or more first vibrations are determined based on one or more dimensions, masses, rigidities, centers of mass, or moments of inertia of the linkage.

4. The system of claim 1, wherein the processor is further configured to:
sense one or more second vibrations in the linkage due to the driving of the linkage to move according to the movement profile; and
mitigate, using the damper, the one or more second vibrations.

5. The system of claim 4, wherein to mitigate the one or more second vibrations, the processor is configured to adjust a variable portion of the damper.

6. The system of claim 1, wherein:
the linkage is configured to support an instrument; and
the movement command indicates a movement of the instrument from a first position to a second position.

7. The system of claim 6, wherein driving the linkage according to the movement profile moves the instrument from the first position to the second position.

8. The system of claim 1, wherein the damper comprises one or more of:
a spring element;
a variable damping element;
an axial flexure;
a top plate and a bottom plate connected by the axial flexure;
a radial flexure coupled to the top plate;
a decoupling flexure positioned between the axial flexure and the radial flexure; or
a shaft connected to the top plate by a ball pivot.

9. The system of claim 1, wherein the damper comprises a plurality of variable damping elements radially positioned around the damper.

10. The system of claim 9, wherein at least one of the plurality of variable damping elements comprises a coil-over damper.

11. The system of claim 1, wherein the damper comprises a plurality of interdigitated protrusions.

12. A method of controlling movement of a system comprising a linkage having a first link, a second link, and a damper coupling the first link to the second link, the method comprising:
receiving, by a processor, a movement command for moving the linkage;
determining, by the processor, one or more first vibrations expected to occur in the linkage as a result of performing the movement command;
determining, by the processor, a movement profile for moving the linkage to reduce the one or more first vibrations; and
driving, by the processor using a drive component, the linkage to move according to the movement profile.

13. The method of claim 12, wherein determining the one or more first vibrations comprises determining one or more forces, accelerations, or jerks that are expected to occur in the linkage as a result of performing the movement command.

14. The method of claim 12, wherein the one or more first vibrations are determined based on one or more dimensions, masses, rigidities, centers of mass, or moments of inertia of the linkage.

15. The method of claim 12, further comprising:
sensing, by the processor, one or more second vibrations in the linkage due to the driving of the linkage to move according to the movement profile; and
mitigating, by the processor using the damper, the one or more second vibrations.

16. The method of claim 15, wherein mitigating the one or more second vibrations comprises adjusting a variable portion of the damper.

17. The method of claim 12, wherein:
the linkage is configured to support an instrument; and
the movement command indicates a movement of the instrument from a first position to a second position.

18. The method of claim 17, wherein driving the linkage according to the movement profile moves the instrument from the first position to the second position.

19. A non-transitory tangible media storing computer-readable instructions, which when executed by a processor, cause the processor to perform a method comprising:
receiving a movement command for moving a linkage, the linkage comprising a first link, a second link, and a damper coupling the first link to the second link;
determining one or more first vibrations expected to occur in the linkage as a result of performing the movement command;
determining a movement profile for moving the linkage to reduce the one or more first vibrations; and
driving, using a drive component, the linkage to move according to the movement profile.

20. The non-transitory tangible media of claim 19, wherein the method further comprises:
sensing one or more second vibrations in the linkage due to the driving of the linkage to move according to the movement profile; and
mitigating, using the damper, the one or more second vibrations.

* * * * *